United States Patent
Sonenshein

(10) Patent No.: US 8,202,695 B2
(45) Date of Patent: Jun. 19, 2012

(54) COMPOSITIONS, METHODS AND KITS FOR REPRESSING VIRULENCE IN GRAM POSITIVE BACTERIA

(75) Inventor: Abraham L. Sonenshein, Brookline, MA (US)

(73) Assignee: Tufts University, Boston, MA (US)

( * ) Notice: Subject to any disclaimer, the term of this patent is extended or adjusted under 35 U.S.C. 154(b) by 954 days.

(21) Appl. No.: 11/710,339

(22) Filed: Feb. 23, 2007

(65) Prior Publication Data

US 2007/0142318 A1 Jun. 21, 2007

Related U.S. Application Data

(63) Continuation-in-part of application No. PCT/US2005/030087, filed on Aug. 24, 2005.

(60) Provisional application No. 60/604,371, filed on Aug. 25, 2004.

(51) Int. Cl.
*A61K 31/7076* (2006.01)
(52) U.S. Cl. ............. 435/6.13; 435/29; 435/32; 514/46
(58) Field of Classification Search .................. None
See application file for complete search history.

(56) References Cited

U.S. PATENT DOCUMENTS

| | | | | |
|---|---|---|---|---|
| 3,094,460 A | * | 6/1963 | De Boer et al. | 424/118 |
| 4,511,653 A | * | 4/1985 | Play et al. | 435/68.1 |
| 5,223,409 A | | 6/1993 | Ladner et al. | |
| 5,288,497 A | * | 2/1994 | Stanley et al. | 424/440 |
| 5,403,484 A | | 4/1995 | Ladner et al. | |
| 5,418,222 A | * | 5/1995 | Song et al. | 424/443 |
| 5,965,125 A | * | 10/1999 | Mineau-Hanschke | 424/93.21 |
| 2003/0040049 A1 | * | 2/2003 | Guedon et al. | 435/69.1 |
| 2003/0171563 A1 | * | 9/2003 | McNamara | 536/23.1 |
| 2003/0228691 A1 | * | 12/2003 | Lewis et al. | 435/375 |
| 2004/0214208 A1 | * | 10/2004 | Ausubel et al. | 435/6 |
| 2005/0059018 A1 | * | 3/2005 | Rahme et al. | 435/6 |
| 2006/0040279 A1 | * | 2/2006 | Feesche et al. | 435/6 |
| 2007/0243303 A1 | * | 10/2007 | Dan Hengst et al. | 426/582 |
| 2007/0244059 A1 | * | 10/2007 | Karaolis | 514/44 |

OTHER PUBLICATIONS

Guedon, Eric e tal, Molecular Microbiology, 2001, vol. 40(5), pp. 1227-1239, Pleiotropic transcriptional repressor CodY senses the intracellular pool of branched-chain amino acids in *Lactococcus lactis*.*

Tempest, D.W. et al, The effect of metabolite analogues on Growth of *Bacillus anthracis* in the Guinea pig and on the Fomation of virulence-determining Factors,. Journal of General Microbiology, vol. 17, 1957, pp. 789-749.* van Schaik, Willem et al, Infection and Immunity, Oct. 2009, vol. 77(10), pp. 4437-4445, The Global Regulator Cody regulates toxin gene expression in *Bacillus anthracis* and is required for Full virulence.*

Inaoka, T et al, Journal of Biological Chemistry, vo. 278(4), Jan. 24, 2003, pp. 2169-2176, Guanine Nucleotides Guanosine 5'-Diphosphate 3'Diphosphate and GTP Co-operatively Regulate the Production of an Antibiotic Bacilysin in *Bacillus subtilis*.*

(Continued)

*Primary Examiner* — Albert Navarro
*Assistant Examiner* — Ginny Portner
(74) *Attorney, Agent, or Firm* — Lawson & Weitzen, LLP; Sonia K. Guterman; Teofilo Javier, Jr.

(57) ABSTRACT

Bacterial virulence is repressed by compositions and methods for activating permanently a repressor of virulence factors. Compositions provided contain at least one non-metabolizable analog of guanine, guanosine, isoleucine and valine.

10 Claims, 11 Drawing Sheets

OTHER PUBLICATIONS

Goyache, J et al, Emerging Infectious Diseases, vol. 7(5), Sep.-Oct. 1991, *Lactococcus lactis* subsp. lactis Infection in Waterfowl: First Confirmation in Animals.*
Facklam, Richard et al, Clinical Microbiology Reviews, Oct. 1995, vol. 8(4), pp. 479-495, Identification, Classification, and Clinical Relevance of Catalase-Negative, Gram Positive Cocci, Excluding Streptococci and Enterococci.*
Sissler, M et al, PNAS, USA, vol. 96, pp. 8985-8990, Aug. 1999, Biochemistry.*
Poolman & Koning, 1988, Journal of Bacteriology, vol. 170(2), pp. 700-707.*
Shivers, Robert P et al, Molcular Microbiolgy, vol. 53(2), pp. 599-611, 2004, Activation of the *Bacillus subitlis* global regulator CodY by direct interaction with branched-chain amino acids, published on line Jun. 22, 2004.*
Bergara, F et al, Journal of Bacteriology, May 2003, pp. 3118-3126, vol. 185(10), CodY is a nutritional repressor of Flagellar Gene Expression in *Bacillus subtilis*.*
Atkinson, M. et al., 1990. J. Bacteriol. 172:4758-4765.
Bai, U. et al., 1993. Genes Dev. 7:139-148.
Belitsky, B. et al., 1997. J. Bacteriol. 179:5448-5457.
Beloin, C. et al., 2000. J. Bacteriol. 182:4414-4424.
Bhavsar, A. et al., 2001. Appl. Environ. Microbiol. 67:403-410.
Blagova, E. et al., 2003. Acta. Cryst. D59:155-157.
Bourne, H. et al., 1991. Nature. 349:117-127.
Braun, V. et al., 1996. Gene 181:29-38.
Bryan, J., 1977. Anal. Biochem. 78:513-519.
Burbulys, D. et al., 1991. Cell 64:545-552.
Burkholder, W. et al., 2001. Cell 104:269-279.
Caldwell, R. et al., 2001. J. Bacteriol. 183:7329-7340.
Cheggour, A. et al., 2000. Mol. Microbiol. 38:504-513.
Craig, J. et al., 1997. J. Bacteriol. 179:7351-7539.
Dartois, V. et al., 1997. Mol. Microbiol. 25:39-51.
Debarbouille, M. et al., 1999. J. Bacteriol. 181:2059-2066.
Den Hengst et al., J. Biol. Chem. Jul. 21, 2005 epub ahead of print as manuscript M502349200.
Dingman, D. et al., 1987. J. Bacteriol. 169:3068-3075.
Dupuy, B. et al., 1998. Mol. Microbiol. 27:107-120.
Eymann, C. et al., 2002. J. Bacteriol. 184:2500-2520.
Ferson, A. et al., 1996. Mol. Microbiol. 22:693-701.
Fisher, S. et al., 1996. J. Bacteriol. 178:3779-3784.
Fouet, A. et al., 1990. J. Bact. 172:5408-5415.
Fouet, A. et al., 1990. J. Bacteriol. 172:835-844.
Freese, E. et al., 1979. J. Gen. Microbiol. 115:193-205.
Freese, E. et al., 1979. Mol. Gen. Genet. 170:67-74.
Gonzalez-Pastor, J. et al., 1995. J. Bacteriol. 177(24):7131-7140.
Grandoni, J. et al., 1993. J. Bacteriol. 175(23):7581-7593.
Grossman, A. et al., 1988. Proc. Natl. Acad. Sci. U.S.A. 85(12):4369-4373.
Grossman, A., 1995. Annu. Rev. Genet. 29:477-508.
Guedon, E. et al., 2001. J. Bacteriol. 183(12):3614-3622.
Guedon, E. et al., 2001. Mol. Microbiol. 40:1227-1239.
Hoch, J., 1993. Annu. Rev. Microbiol. 47:441-465.
Inaoka, T. et al., 2002. J. Bacteriol. 184:3923-3930.
Ireton, K. et al., 1993. Genes Dev. 7:283-294.
Ireton, K. et al., 1994. J. Bacteriol. 176:5320-5329.
Ishikawa, S. et al., 2002. J. Biol. Chem. 277:20483-20489.
Jin, S. et al., 1996. J. Bacteriol. 178:3658-3660.
Joseph, P. et al., 2005. J. Bacteriol. 187:4127-4139.
Jourlin-Castelli, C. et al., 2000. J. Mol. Biol. 295:865-878.
Kim, H. et al., 2003. J. Bacteriol. 185:1672-1680.
Koide, A. et al., 1999. J. Bacteriol. 181:4114-4117.
Lazazzera, B. et al., 1997. Cell 89:917-925.
Ledeaux, J. et al., 1995. J. Bacteriol. 177:861-863.
Levkdikov, V. M. et al. 2006. Journal of Biological Chemistry 281:11366-11373.
Lopez, J. et al., 1979. Biochim. Biophys. Acta. 587:238-252.
Lopez, J. et al., 1981. J. Bacteriol. 146:605-613.
Mani, N. et al., 2001. Proc. Natl. Acad. Sci. U.S.A. 98:5844-5849.
Mani, N. et al., 2002. J. Bacteriol. 184(51):5971-5978.
Mathiopoulos, C. et al., 1989. Mol. Microbiol. 3:1071-1081.
Mathiopoulos, C. et al., 1991. Mol. Microbiol. 5:1903-1913.
Mauck et al., 1971. J. Biol. Chem. 246:1820-1827.
Mirel, D. et al., 2000. J. Bacteriol. 182:3055-3062.
Mitani, T. et al., 1977. Biochim. Biophys. Acta. 77:1118-1125.
Molle, V. et al., 2003. J. Bacteriol. 185:1911-1922.
Moncrief, J. et al., 1997. Infect. Immun. 65(3):1105-1108.
Mueller, J. et al., 1992. J. Bacteriol. 174:4374-4383.
Ochi, K. et al., 1981. J. Biol. Chem. 256(13):6866-6875.
Ohne, M., 1974. J. Bacteriol. 117(3)1295-1305.
Park, J., 1995. Mol. Microbiol. 17:421-426.
Perego, M. et al., 1994. Cell 79:1047-1055.
Perego, M. et al., 1996. Proc. Natl. Acad. Sci. U.S.A. 93:1549-1553.
Perego, M., 1997. Proc. Natl. Acad. Sci. U.S.A. 94:8612-8617.
Petranovic, D. et al., 2004. Mol. Microbiol. 53:613-621.
Quisel, J. et al., 2000. J. Bacteriol. 182:3446-3451.
Ratnayake-Lecamwasam, M. et al., 2001. Genes Dev. 15:1093-1103.
Rosenkrantz, M. et al., 1985. J. Bacteriol. 164:155-164.
Schmidt, D. et al., 2001. Biochemistry 40:15707-15715.
Serror, P. et al., 1996. J. Bacteriol. 178:5910-5915.
Serror, P. et al., 1996. Mol. Microbiol. 20:843-852.
Shivers, R. and A.L. Sonenshein, 2005 Molec. Microbiol. 56:1549-1559.
Shivers, R. et al., 2004. Mol. Microbiol. 53:599-611.
Slack, F. et al., 1991. Mol. Microbiol. 5:1915-1925.
Slack, F. et al., 1993. J. Bacteriol. 175:4605-4614.
Slack, F. et al., 1995. Mol. Microbiol. 15:689-702.
Steiner, K. et al., 2001. J. Bacteriol. 183:7354-7364.
Strauch, M. et al., 1995. Mol. Gen. Genet. 246:756-760.
Wendrich, T. et al., 1997. Mol. Microbiol. 26:65-79.
Wray, L. et al., 1997. J. Bacteriol. 179:5494-5501.
Xu, K. et al., 1996. Mol. Microbiol. 19:145-158.
Zwieb, C. et al., 1989. Genes Dev. 3:606-611.

* cited by examiner

*C. botulinum* toxin gene locus botR/A2  p47  ntnh  bont/A2

0 100 400 500
CodY (nM)

Fig. 11

SEQUENCE LISTING

```
<160> NUMBER OF SEQ ID NOS: 40

<210> SEQ ID NO 1
<211> LENGTH: 20
<212> TYPE: DNA
<213> ORGANISM: Artificial sequence
<220> FEATURE:
<223> OTHER INFORMATION: The nucleic acid was designed and synthesized
<220> FEATURE:
<221> NAME/KEY: misc_feature
<222> LOCATION: (3)..(4)
<223> OTHER INFORMATION: n is a, c, g, or t

<400> SEQUENCE: 1
cannattttt taaaaattat                                              20

<210> SEQ ID NO 2
<211> LENGTH: 20
<212> TYPE: PRT
<213> ORGANISM: Bacillus subtilis
<220> FEATURE:
<221> NAME/KEY: misc_feature
<223> OTHER INFORMATION: Bacillus subtilis CodY HTH motif

<400> SEQUENCE: 2

Ala Ser Lys Ile Ala Asp Arg Val Gly Ile Thr Arg Ser Val Ile Val
1               5                   10                  15

Asn Ala Leu Arg
            20

<210> SEQ ID NO 3
<211> LENGTH: 20
<212> TYPE: PRT
<213> ORGANISM: Listeria monocytogenes
<220> FEATURE:
<221> NAME/KEY: misc_feature
<223> OTHER INFORMATION: Listeria monocytogenes CodY HTH motif

<400> SEQUENCE: 3

Ala Ser Lys Ile Ala Asp Arg Val Gly Ile Thr Arg Ser Val Ile Val
1               5                   10                  15

Asn Ala Leu Arg
            20

<210> SEQ ID NO 4
<211> LENGTH: 20
<212> TYPE: PRT
<213> ORGANISM: Staphylococcus aureus
<220> FEATURE:
<221> NAME/KEY: misc_feature
```

```
<223> OTHER INFORMATION: Staphylococcus aureus CodY HTH motif

<400> SEQUENCE: 4

Ala Ser Lys Val Ala Asp Arg Val Gly Ile Thr Arg Ser Val Ile Val
1               5                   10                  15

Asn Ala Leu Arg
            20

<210> SEQ ID NO 5
<211> LENGTH: 20
<212> TYPE: PRT
<213> ORGANISM: Clostridium difficile
<220> FEATURE:
<221> NAME/KEY: misc_feature
<223> OTHER INFORMATION: Clostridium difficile CodY HTH motif

<400> SEQUENCE: 5

Ala Ser Lys Ile Ala Asp Arg Val Gly Ile Thr Arg Ser Val Ile Val
1               5                   10                  15

Asn Ala Leu Arg
            20

<210> SEQ ID NO 6
<211> LENGTH: 20
<212> TYPE: PRT
<213> ORGANISM: Streptococcus pneumoniae
<220> FEATURE:
<221> NAME/KEY: misc_feature
<223> OTHER INFORMATION: Streptococcus pneumoniae CodY HTH motif

<400> SEQUENCE: 6

Ala Ser Val Ile Ala Asp Arg Ile Gly Ile Thr Arg Ser Val Ile Val
1               5                   10                  15

Asn Ala Leu Arg
            20

<210> SEQ ID NO 7
<211> LENGTH: 8
<212> TYPE: PRT
<213> ORGANISM: Escherichia coli

<400> SEQUENCE: 7

Leu Gly Gly Gly Thr Gly Thr Gly
1               5

<210> SEQ ID NO 8
<211> LENGTH: 4
<212> TYPE: PRT
<213> ORGANISM: Escherichia coli

<400> SEQUENCE: 8

Asp Ala Phe Gly
1

<210> SEQ ID NO 9
<211> LENGTH: 4
<212> TYPE: PRT
<213> ORGANISM: Escherichia coli

<400> SEQUENCE: 9

Thr Ser Leu Asp
1

<210> SEQ ID NO 10
<211> LENGTH: 8
```

```
<212> TYPE: PRT
<213> ORGANISM: Bacillus subtilis

<400> SEQUENCE: 10

Gly Gly Glu Arg Leu Gly Thr Leu
1               5

<210> SEQ ID NO 11
<211> LENGTH: 4
<212> TYPE: PRT
<213> ORGANISM: Bacillus subtilis

<400> SEQUENCE: 11

Asp Arg Val Gly
1

<210> SEQ ID NO 12
<211> LENGTH: 7
<212> TYPE: PRT
<213> ORGANISM: Bacillus subtilis

<400> SEQUENCE: 12

Val Leu Asn Asn Lys Phe Leu
1               5

<210> SEQ ID NO 13
<211> LENGTH: 7
<212> TYPE: PRT
<213> ORGANISM: Bacillus stearothermophilus

<400> SEQUENCE: 13

Val Leu Asn Asp Lys Phe Leu
1               5

<210> SEQ ID NO 14
<211> LENGTH: 8
<212> TYPE: PRT
<213> ORGANISM: Bacillus halodurans

<400> SEQUENCE: 14

Gly Gly Gln Arg Leu Gly Thr Leu
1               5

<210> SEQ ID NO 15
<211> LENGTH: 7
<212> TYPE: PRT
<213> ORGANISM: Staphylococcus aureus

<400> SEQUENCE: 15

Val Lys Lys Glu Lys Phe Leu
1               5

<210> SEQ ID NO 16
<211> LENGTH: 7
<212> TYPE: PRT
<213> ORGANISM: Staphylococcus epidermidis

<400> SEQUENCE: 16

Val Lys Lys Asp Lys Phe Leu
1               5

<210> SEQ ID NO 17
<211> LENGTH: 8
<212> TYPE: PRT
<213> ORGANISM: Carboxydothermus hydrogenoformans
```

```
<400> SEQUENCE: 17

Gly Gly Val Arg Leu Gly Thr Leu
1               5

<210> SEQ ID NO 18
<211> LENGTH: 7
<212> TYPE: PRT
<213> ORGANISM: Carboxydothermus hydrogenoformans

<400> SEQUENCE: 18

Ile Leu Asn Asp Tyr Phe Leu
1               5

<210> SEQ ID NO 19
<211> LENGTH: 8
<212> TYPE: PRT
<213> ORGANISM: Desulfitobacterium hafniense

<400> SEQUENCE: 19

Gly Gly Glu Arg Val Gly Thr Leu
1               5

<210> SEQ ID NO 20
<211> LENGTH: 7
<212> TYPE: PRT
<213> ORGANISM: Desulfitobacterium hafniense

<400> SEQUENCE: 20

Asp Leu Asn Asp Tyr Leu Leu
1               5

<210> SEQ ID NO 21
<211> LENGTH: 8
<212> TYPE: PRT
<213> ORGANISM: Streptococcus pneumoniae

<400> SEQUENCE: 21

Ser Gly Ile Arg Leu Gly Ser Leu
1               5

<210> SEQ ID NO 22
<211> LENGTH: 4
<212> TYPE: PRT
<213> ORGANISM: Streptococcus pneumoniae

<400> SEQUENCE: 22

Asp Arg Ile Gly
1

<210> SEQ ID NO 23
<211> LENGTH: 7
<212> TYPE: PRT
<213> ORGANISM: Streptococcus pneumoniae

<400> SEQUENCE: 23

Val Leu Ile Ser Asp Ile Phe
1               5

<210> SEQ ID NO 24
<211> LENGTH: 8
<212> TYPE: PRT
<213> ORGANISM: Streptococcus equi

<400> SEQUENCE: 24

Gly Gly Met Arg Leu Gly Thr Leu
```

-continued

<210> SEQ ID NO 25
<211> LENGTH: 7
<212> TYPE: PRT
<213> ORGANISM: Streptococcus equi

<400> SEQUENCE: 25

Val Ile Asn Glu Gly Ile Phe
1               5

<210> SEQ ID NO 26
<211> LENGTH: 8
<212> TYPE: PRT
<213> ORGANISM: Streptococcus mutans

<400> SEQUENCE: 26

Gly Gly Met Arg Leu Gly Ser Leu
1               5

<210> SEQ ID NO 27
<211> LENGTH: 8
<212> TYPE: PRT
<213> ORGANISM: Enterococcus faecalis

<400> SEQUENCE: 27

Ala Gly Lys Arg Leu Gly Thr Ile
1               5

<210> SEQ ID NO 28
<211> LENGTH: 4
<212> TYPE: PRT
<213> ORGANISM: Enterococcus faecalis

<400> SEQUENCE: 28

Asp Glu Ile Gly
1

<210> SEQ ID NO 29
<211> LENGTH: 7
<212> TYPE: PRT
<213> ORGANISM: Enterococcus faecalis

<400> SEQUENCE: 29

Val Leu Asn Gln Gln Phe Ile
1               5

<210> SEQ ID NO 30
<211> LENGTH: 8
<212> TYPE: PRT
<213> ORGANISM: Lactobacillus lactis

<400> SEQUENCE: 30

Ser Gly Met Arg Leu Gly Thr Phe
1               5

<210> SEQ ID NO 31
<211> LENGTH: 4
<212> TYPE: PRT
<213> ORGANISM: Lactobacillus lactis

<400> SEQUENCE: 31

Asp Lys Ile Gly
1

```
<210> SEQ ID NO 32
<211> LENGTH: 7
<212> TYPE: PRT
<213> ORGANISM: Lactobacillus lactis

<400> SEQUENCE: 32

Val Leu Asn Thr Gly Leu Phe
1               5

<210> SEQ ID NO 33
<211> LENGTH: 8
<212> TYPE: PRT
<213> ORGANISM: Clostridium difficile

<400> SEQUENCE: 33

Ser Gly Gln Arg Leu Gly Thr Leu
1               5

<210> SEQ ID NO 34
<211> LENGTH: 7
<212> TYPE: PRT
<213> ORGANISM: Clostridium difficile

<400> SEQUENCE: 34

Ile Leu Asn Asp Lys Leu Thr
1               5

<210> SEQ ID NO 35
<211> LENGTH: 8
<212> TYPE: PRT
<213> ORGANISM: Clostridium perfringens

<400> SEQUENCE: 35

Asn Gly Asp Arg Leu Gly Thr Leu
1               5

<210> SEQ ID NO 36
<211> LENGTH: 4
<212> TYPE: PRT
<213> ORGANISM: Clostridium perfringens

<400> SEQUENCE: 36

Asp Lys Val Gly
1

<210> SEQ ID NO 37
<211> LENGTH: 7
<212> TYPE: PRT
<213> ORGANISM: Clostridium perfringens

<400> SEQUENCE: 37

Ile Leu Asn Glu Lys Leu Met
1               5

<210> SEQ ID NO 38
<211> LENGTH: 8
<212> TYPE: PRT
<213> ORGANISM: Clostridium acetobutylicum

<400> SEQUENCE: 38

Asn Arg Glu Arg Leu Gly Thr Leu
1               5

<210> SEQ ID NO 39
<211> LENGTH: 7
<212> TYPE: PRT
```

```
<213> ORGANISM: Clostridium acetobutylicum

<400> SEQUENCE: 39

Ile Leu Asn Asp Arg Leu Leu
1               5

<210> SEQ ID NO 40
<211> LENGTH: 7
<212> TYPE: PRT
<213> ORGANISM: Clostridium botulinum

<400> SEQUENCE: 40

Ile Leu Asn Asp Lys Leu Leu
1               5
```

COMPOSITIONS, METHODS AND KITS FOR REPRESSING VIRULENCE IN GRAM POSITIVE BACTERIA

RELATED APPLICATION

This application is a continuation-in-part of and claims the benefit of PCT/US2005/030087 filed Aug. 24, 2005 in the PCT Receiving Office of the U.S. Patent and Trademark Office, which claims the benefit of provisional application 60/604,371 filed Aug. 25, 2004 in the U.S. Patent and Trademark Office, both of which are hereby incorporated by reference herein in their entirety.

GOVERNMENT SUPPORT

This invention was made with government support under grants GM042219 and AI057637 awarded by the National Institutes of Health. The government has certain rights in the invention.

FIELD OF THE INVENTION

The present invention relates to regulation of expression of pathogenicity genes in Gram positive pathogenic bacterial strains.

BACKGROUND

The ability to grow by using a multitude of potential nutritional sources is a hallmark of the bacterial world. As a result, a goal of microbial physiology is obtaining an understanding of how microorganisms sense alterations in their environment, and how they respond rapidly and efficiently. Bacteria adapt readily and efficiently and have evolved very sensitive means of monitoring changes in their intracellular pools or in their immediate environments and highly sophisticated mechanisms for translating those signals into changes in gene expression.

Sporulation is a special case of adaptation to nutrient limitation. It is general in the sense that limitation of any of sources of carbon, nitrogen or phosphorus can induce sporulation, but the decision to sporulate in no way ameliorates the stress-inducing condition (Sonenshein, A. L., 2000. In: Bacterial stress responses, G. Storz et al. (eds.), ASM Press, Washington, D.C., pp. 199-215). Instead the sporulating cell gives up on growth in order to create within itself a protected environment for its genome. While the spore is highly resistant to many forms of environmental stress (e.g., heat, desiccation, large variations in pH, organic solvents, osmotic imbalance, antibiotics), spore formation is not triggered by any of the stresses to which resistance is gained. The specific metabolic signal to which cells respond when making the decision to sporulate and the mechanism by which the signal is recognized remain incompletely characterized (Sonenshein, A. L., 1989. In: Regulation of procaryotic development, I. Smith et al. (eds.), ASM Press, Washington, D.C., pp. 109-130). Freese and colleagues showed that a drop in the intracellular pools of GDP and GTP correlates with the onset of sporulation (Freese, E. et al., 1979. J. Gen. Microbiol. 115:193-205; Lopez, J. et al., 1981. J. Bacteriol. 146:605-61; Lopez, J. et al., 1979. Biochim. Biophys. Acta. 587:238-252; Mitani, T. et al., 1977. Biochim. Biophys. Acta. 77:1118-1125; Ochi, K. et al., 1981. J. Biol. Chem. 256:6866-6875). Moreover, limitation of guanine nucleotide synthesis, by treatment with an inhibitor or by limitation of a purine auxotroph, induces sporulation in cultures growing in excess nutrients (Freese, E. et al., 1979. J. Gen. Microbiol. 115:193-205; Freese, E. et al., 1979. Mol. Gen. Genet. 170:67-74; Mitani, T. et al., 1977. Biochim. Biophys. Acta. 77:1118-1125), as if the nutritional signal that cells monitor is the concentration of GDP and/or GTP. Nucleotides are exemplary as signal compounds because their synthesis depends on adequate supplies of carbon, nitrogen and phosphorus.

For many years researchers have sought the *B. subtilis* proteins that sense nutrient limitation and, more specifically, GTP availability. Recent evidence indicates that CodY, a GTP binding protein, is a factor in this regulation (Ratnayake-Lecamwasam, M. et al., 2001. Genes Dev. 15:1093-1103). In fact, GTP activates CodY as a repressor (Ratnayake-Lecamwasam, M. et al., 2001). CodY was first identified as a negative regulator of the dipeptide permease (dpp) operon (Slack, F. et al., 1993. J. Bacteriol. 175:4605-4614; Slack, F. et al., 1995. Mol. Microbiol. 15:689-702), and was subsequently found to repress during rapid exponential growth phase a group of genes whose products are generally involved in adaptation to poor growth conditions. The targets of CodY include genes that encode extracellular degradative enzymes, transport systems, catabolic pathways, genetic competence, antibiotic synthesis, flagellin, and sporulation functions (Burkholder, W. et al., 2000. In: *Prokaryotic development*, Y. Brun et al. (eds.), ASM Press, Washington D.C., pp. 151-166; Debarbouille, M. et al., 1999. J. Bacteriol. 181:2059-2066; Ferson, A. et al., 1996. Mol. Microbiol. 22:693-701; Fisher, S. et al., 1996. J. Bacteriol. 178:3779-3784; Mirel, D. et al., 2000. J. Bacteriol. 182:3055-3062; Serror, P. et al., 1996. J. Bacteriol. 178:5910-5915; Slack, F. et al., 1993. J. Bacteriol. 175:4605-4614; Slack, F. et al., 1995. Mol. Microbiol. 15:689-702; Wray, L. et al., 1997. J. Bacteriol. 179:5494-5501; Molle, V. et al., 2003. J. Bacteriol. 185:1911-1922; Kim, H. et al., 2003. J. Bacteriol. 185:1672-1680).

Although unrelated to other families of regulatory proteins, homologs of CodY are generally found in the low G+C family of Gram positive bacteria, including *Bacillus anthracis, B. halodurans, B. stearothermophilus, Clostridium perfringens, C. difficile, C. acetobutylicum, C. botulinum, Staphylococcus aureus, S. epidermidis, Streptococcus pneumoniae, S. agalactiae, S. pyogenes, S. equi, S. mutans, Listeria monocytogenes, L. innocua, Desulfitobacterium hafniense, Carboxydothermus hydrogenoformans, Lactococcus lactis,* and *Enterococcus faecalis.* This group includes major human and animal pathogens and important industrial bacteria.

With recent increases in antibiotic resistance in bacteria, there is a need for compositions and methods for regulating production of toxins and other materials involved in disease by Gram positive pathogens.

SUMMARY

A featured embodiment of the invention provided herein is a composition for repressing virulence in a Gram positive bacterium, the composition comprising an effective concentration of at least one of a branched chain amino acid or an analog thereof and a cell-permeable precursor or analog of guanosine triphosphate (GTP), and a pharmaceutically acceptable salt or buffer, such that the concentration is effective to repress virulence of the bacterium. Accordingly, the branched chain amino acid is isoleucine or an analog thereof, or valine or an analog thereof. Further, the precursor of GTP is guanosine or an analog thereof, or guanine or an analog thereof, or an inosine or an analog thereof.

An effective concentration of the branched chain amino acid is at least about 5 mM. Alternatively, the effective concentration of the branched chain amino acid is at least about 10 mM. An effective concentration of the guanine, guanosine, or analog thereof is at least about 0.5 mM. Alternatively, the effective concentration of the guanine, guanosine, or analog thereof is at least about 1 mM. The effective concentration of the branched chain amino acid, guanine, guanosine, or analog thereof is less than about 50 mM. For example, the effective concentration of the branched chain amino acid, guanine, guanosine, or analog thereof is less than about 20 mM. Exemplary branched chain amino acid analogs for testing for ability to bind to and modulate activity of CodY are selected from isovaleric acid, 2-hydroxyisovaleric acid, 2-ketoisovaleric acid, isovaleral, 2-aminobutyric acid, valinol, 2-hydroxy-3-methylvaleric acid, 2-keto-3-methylvaleric acid, 3-methylvaleric acid, 3-methylvaleral, D-valine, and D-isoleucine.

Another featured embodiment provided herein is a method for identifying an agent for decreasing expression of virulence factors in Gram positive bacteria, the method comprising:

contacting a first sample of the bacteria with an analog of guanine, guanosine, isoleucine or valine at a concentration capable of activating repression by CodY; and analyzing expression of a CodY-regulated gene product, wherein decreased expression of the gene product compared to expression of the gene product in a second sample of bacteria not so contacted and otherwise identical identifies the analog as an agent for limiting expression of virulence factors in Gram positive bacteria.

A related embodiment of the method further includes analyzing expression of the gene product in a third sample of the bacteria contacted with isoleucine and guanine or guanosine which is a positive control, such that decreased expression in the first sample and third sample compared to the second sample further identifies the analog as the agent. For example, expression in the first sample is less than about 25% of that in the second sample, or is less than about 50% of that in the second sample, or is less than about 75% of that in the second sample.

In general for the method, the sample is a culture of a species of a bacterium that expresses a CodY-like protein, for example, the sample is a culture of a species of a low G+C DNA content Gram positive bacterium. Thus, the sample is a culture of a species of a *Bacillus*, a *Clostridium*, a *Listeria*, a *Staphylococcus*, a *Streptococcus*, a *Desulfitobacterium*, a *Carboxydothermus*, an *Enterococcus*, a *Lactococcus*, or a *Lactobacillus*. Further, in the embodiment that the genus is *Bacillus*, the species is selected from the group consisting of *B. subtilis, B. anthracis, B. cereus, B. popilliae, B. halodurans, B. stearothermophilus* and *B. thuringiensis*.

In general for the method, the CodY-regulated gene product is an RNA or a protein. For example, the RNA is an mRNA. In certain embodiments of the method, the mRNA is a transcript of a gene selected from dppA and ilvB. Further the CodY-regulated gene product is a genetic fusion to a marker gene, for example, the marker gene is selected from any of a gene encoding a β-galactosidase, a β-glucuronidase, an alkaline phosphatase and a fluorescent protein.

Another featured embodiment of the invention herein is a method for identifying an agent for decreasing expression of virulence factors in Gram positive bacteria, the method including:

contacting a first sample of a CodY protein with an analog of at least one of isoleucine, valine, and GTP in the presence of a target nucleic acid; and analyzing binding of the CodY protein to the nucleic acid, such that increased binding of the CodY protein to the target nucleic acid, compared to binding in a second sample of CodY protein absent the analog and otherwise identical, is an indication that the analog is an agent that limits expression of virulence factors.

In various embodiments of the method, the nucleic acid is selected from the group of genes ilvB, ilvD, ybgE, yhdG, yurP, yufN, dpp, sfrAA and comK of *B. subtilis*; tcdR (also known as txeR) of *C. difficile*; ssp, hla and nuc of *S. aureus*; botR of *C. botulinum*; and lef, pag, cya and atxA of *B. anthracis*. In general, the nucleic acid is at least about 20 nucleotides in length. For example, the nucleic acid comprises the nucleotide sequence CANNATTTTTTAAAAATTAT (SEQ ID NO: 1). Alternatively, the nucleic acid comprises a nucleotide sequence that is at least about 95% identical to CANNATTTTTTAAAAATTAT (SEQ ID NO: 1), or is at least about 85% identical to CANNATTTTTTAAAAATTAT (SEQ ID NO: 1), or is at least about 75% identical to CANNATTTTTTAAAAATTAT (SEQ ID NO: 1).

In various embodiments of the method, the gene encoding the CodY protein is obtained from the genome of a Gram positive bacterium, for example, the gene encoding the CodY protein is obtained from a low G+C Gram positive bacterium. Further, the gene encoding the CodY protein can be expressed in a heterologous host cell, for example, the host cell is *Escherichia coli*.

Another featured embodiment of the invention provided herein is a method for decreasing expression of a virulence factor in a Gram positive bacterial cell, the method including contacting the cell with an agent that is a co-repressor of a CodY protein. For example, the agent is an analog of a branched chain amino acid, a guanosine or a guanine. In certain embodiments, the agent is a composition having a plurality of analogs of a branched chain amino acid and analogs of a guanosine or a guanine. In most embodiments, the bacterial cell is a pathogen of a eukaryotic organism, and the organism is a warm-blooded animal, for example, the organism is a mammal, for example, the organism is a human.

Also provided is a kit for identifying an agent for decreasing expression of virulence factors in Gram positive bacteria, comprising a CodY protein, a nucleic acid, a container, and instructions for use. Accordingly, the CodY protein and the nucleic acid each are provided in unit doses.

BRIEF DESCRIPTION OF THE DRAWINGS

FIG. 11 is a photograph of an electrophoretogram gel mobility shift assay showing that *Clostridium difficile* CodY protein interacts with the promoter regions of the *Clostridium botulinum* botR and p47 genes. The numbers beneath each lane indicate the concentration (nM) of CodY protein in each binding reaction. GTP (2 mM) and a mixture of isoleucine, valine and leucine (10 mM each) were included in each reaction.

DETAILED DESCRIPTION OF EMBODIMENTS

Figure 1:
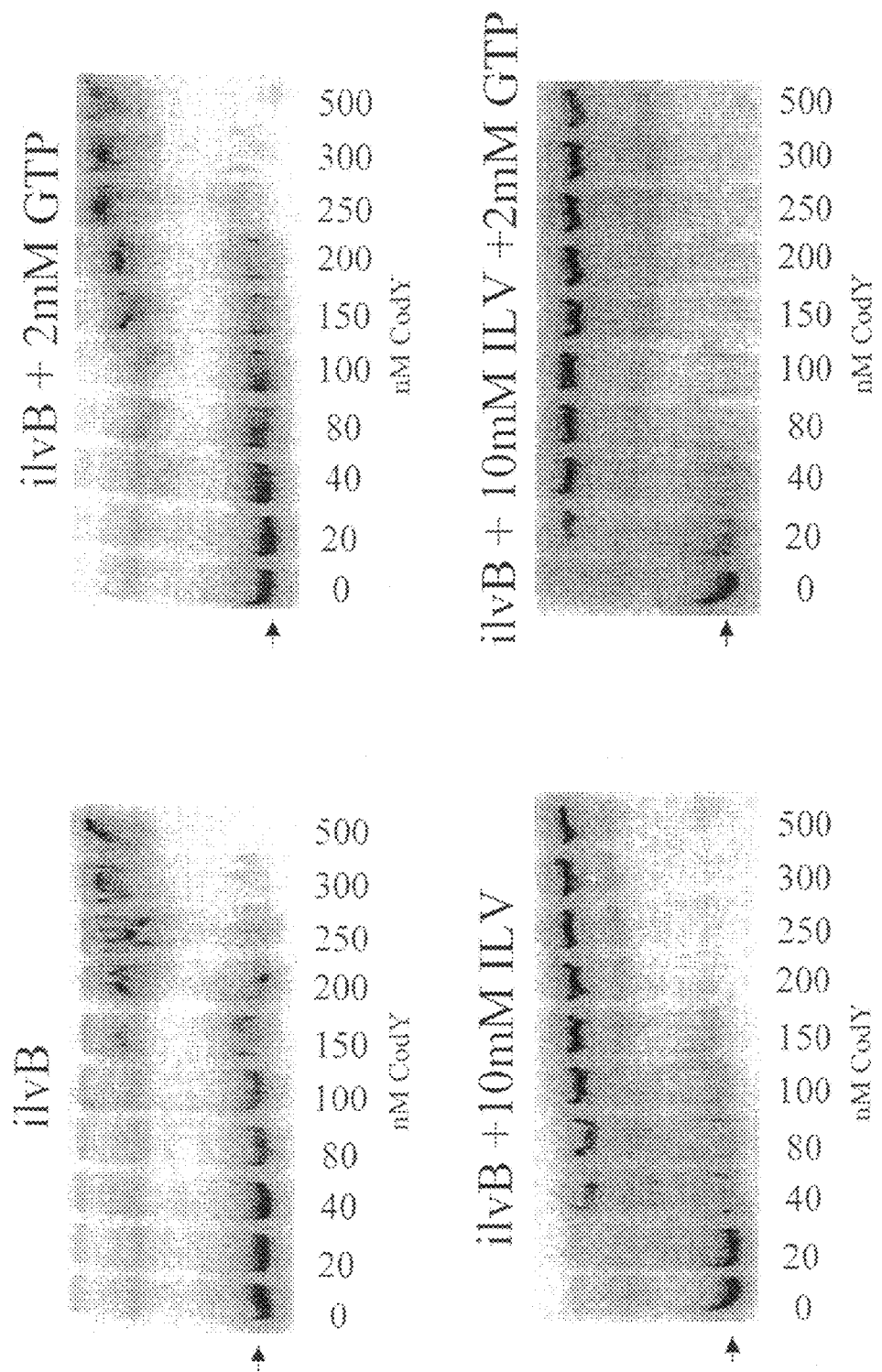
FIG. 1 is a photograph of a gel electrophoretogram of gel shift assays of the ilvB promoter region in the presence of increasing concentrations of CodY and 2 mM GTP or 10 mM Ile-Val-Leu or both. Arrows indicate unshifted probe.

CodY appears to be a cellular monitor of both GTP and branched chain amino acids (Ratnayake-Lecamwasam, M. et al., 2001. Genes Dev. 15:1093-1103; Shivers, R. et al., 2004. Mol. Microbiol. 53:599-611, the contents of which are hereby incorporated by reference herein). Its activity as a transcriptional regulator links general nutrient availability with both stationary phase and early sporulation gene expression. This finding offers a paradigm for how general nutritional sufficiency might be detected in other organisms. Recent work shows that CodY also interacts with branched chain amino acids (BCAAs); isoleucine and valine stimulate binding of CodY to target sites, suggesting that CodY measures two different kinds of nutritional signals (Shivers, R. et al., 2004. Mol. Microbiol. 53:599-611).

In *L. lactis*, CodY is a regulator of genes involved in extracellular proteolysis, peptide uptake and intracellular peptide utilization and may also respond directly to BCAAs (Guedon, E. et al., 2001. Mol. Microbiol. 40:1227-1239; Guedon, E. et al., 2001. J. Bacteriol. 183:3614-3622, but not to GTP (Petranovic, D. et al., 2004. Mol. Microbiol. 53:613-621). It is very likely that the CodY homologs in other low G+C bacteria also control early stationary phase gene expression, but to date there is only indirect evidence to support such a role. In *Streptococcus pyogenes*, for example, a group of metabolic, stress response, quorum sensing, and virulence genes is induced by amino acid starvation by a mechanism that can be independent of the stringent response and could reflect CodY-mediated regulation (Steiner, K. et al., 2001. J. Bacteriol. 183:7354-7364). Since many diverse virulence factors, antibiotics, and useful products are expressed in the stationary phase cells of Gram positive bacteria, there is a high probability that CodY plays a role in controlling their expression. In fact, it is shown herein that the CodY proteins from each of *B. anthracis*, *S. aureus*, and *C. difficile* bind specifically and with high affinity to promoter regions of virulence genes.

Global regulation mechanisms in response to a specific metabolite take many forms in bacteria. The Leucine Responsive Protein (Lrp) of Gram negative bacteria controls a network of genes whose functions touch many aspects of intermediary metabolism, including branched chain amino acid biosynthesis (Mueller, J. et al., 1992. J. Bacteriol. 174:4374-4383) and other varied aspects of cell function (Newman, E. et al., 1996. In: *Escherichia coli and Salmonella*: Cellular and molecular biology, Second edition, F. C. Neidhardt et al. (eds.), ASM Press, Washington, D.C., pp. 1513-1525). In many cases, binding of Lrp to its target sites depends on the presence of leucine. It has been proposed that leucine is a particularly effective indicator of general nutritional capacity because its accumulation depends on many fundamental precursors. For some genes, however, serine rather than leucine is the effector or no apparent effector, is needed. The operons controlled by Lrp need not have any direct or indirect connection with leucine or serine metabolism. This feature distinguishes Lrp from CAP, CcpA, NtrC, and TnrA proteins, all of which respond to carbon-containing or nitrogen-containing compounds for the purpose of regulating utilization of other carbon- or nitrogen-containing compounds. *B. subtilis* encodes seven homologs of Lrp, and its close *E. coli* homolog is known as AsnC. While these proteins have been studied (Belitsky, B. et al., 1997. J. Bacteriol. 179:5448-5457; Beloin, C. et al., 2000. J. Bacteriol. 182:4414-4424; Dartois, V. et al., 1997. Mol. Microbiol. 25:39-51), none appears as yet to have the global activity of Lrp. They seem instead to be operon-specific regulators. CodY has an even broader cellular regulatory role than Lrp, since CodY regulates expression of genes from such diverse groups as anabolic, catabolic, and differentiation pathways. As shown below, the CodY regulon in *B. subtilis* now embraces several hundred genes that are either repressed or are activated by CodY. There is at least preliminary evidence that *B. subtilis* CodY binds to the regulatory regions of about 70 operons that contain many of these genes (Molle, V. et al., 2003. J. Bacteriol. 185:1911-1922). The fact that CodY responds to two types of metabolic molecules, GTP and BCAAs, suggests that it plays a central role in the regulation of metabolism and in the cell's response to nutritional availability.

The stringent response was the first described global system of regulation in bacteria (Cashel, M. et al., 1996. In: *Escherichia coli and Salmonella*: Cellular and molecular biology, Second edition, F. C. Neidhardt et al. (eds.), ASM Press, Washington, D.C., pp. 1458-1496). The stringent response is the term used to describe a cellular mechanism in which, when amino acid limitation becomes severe, cells shut off synthesis of ribosomal RNA and ribosomal proteins while maintaining synthesis of at least some types of mRNA. The signal for this response is the binding of uncharged tRNA to the ribosome and the consequent activation of RelA, a ribosome-bound enzyme that converts GTP to pppGpp. The exact mechanism by which (p)ppGpp changes the rate of transcription of various genes has remained controversial despite decades of research. Direct interaction of (p)ppGpp with RNA polymerase is thought to be responsible for some of its effects.

A stringent response can be induced in *B. subtilis* as in other bacteria (Solomon, J. et al., 1995. Genes Dev. 9:547-558), but given the possible relationships among amino acid limitation, pppGpp synthesis, GTP pool size, and CodY activity, it is probable that some effects attributed to stringency in *B. subtilis* might actually be due to effects on CodY activity. The synthesis of (p)ppGpp not only reduces the GTP pool directly but also leads to a reduction in de novo biosynthesis of GTP via inhibition of IMP dehydrogenase (Ochi, K. et al., 1981. J. Biol. Chem. 256:6866-6875). Thus, when genes are turned on or off by amino acid limitation, they may be responding to a deficit of a specific amino acid or to synthesis of (p)ppGpp, or alternatively, to inactivation of CodY, or to some combination. A study of the role of RelA in genetic competence has given an interesting perspective. A relA mutant is defective in competence, but this defect can be bypassed by limiting GTP synthesis or by deleting codY (Inaoka, T. et al., 2002. J. Bacteriol. 184:3923-3930). The sporulation defect of a relA mutant is also suppressed by a codY mutation (Inaoka, T. et al., 2002). CodY binds to the regulatory regions of two key early competence genes, srfAA and comK (Serror, P. et al., 1996. J. Bacteriol. 178:5910-5915), so the only role of RelA in *B. subtilis* genetic competence appears to be to reduce the GTP pool enough to relieve CodY-mediated repression of early competence genes.

While the decision of a cell to sporulate is based in part on the intracellular pool of GTP, there are other signals that come into play. High population density, thought to be communicated from cell-to-cell by secreted oligopeptides (Burkholder, W. et al., 2000. In: *Prokaryotic development*, Y. Brun et al. (eds.), ASM Press, Washington D.C., pp. 151-166; Grossman, A., 1995. Annu. Rev. Genet. 29:477-508; Grossman, A. et al., 1988. Proc. Natl. Acad. Sci. U.S.A. 85:4369-4373), and the replication state of the chromosome (Burkholder, W. et al., 2000. In: *Prokaryotic development*, Y. Brun et al. (eds.), ASM Press, Washington D.C., pp. 151-166; Burkholder, W. et al., 2001. Cell 104:269-279; Grossman, A., 1995. Annu. Rev. Genet. 29:477-508) are also signals or checkpoints for initiation of sporulation. The role played by Rap phosphatases and their inhibitors (Phr peptides) in mediating the effects of population density (Burkholder, W. et al., 2000. In: *Prokaryotic development*, Y. Brun et al. (eds.), ASM Press, Washington D.C., pp. 151-166; Perego, M., 1997. Proc. Natl. Acad. Sci. U.S.A. 94:8612-8617), include, in early stationary phase cells, simultaneous induction of a potent histidine kinase, KinA, and a phosphatase, RapA (Perego, M., 1997; Perego, M. et al., 1996. Proc. Natl. Acad. Sci. U.S.A. 93:1549-1553; Perego, M. et al., 1994. Cell 79:1047-1055). After autophosphorylation, KinA transfers phosphate to Spo0F, which then serves as a donor for Spo0B-mediated transfer of phosphate to Spo0A, the major transcription factor for early stationary phase gene expression. However, RapA blocks the flow of phosphate to Spo0A by dephosphorylating Spo0F~P (Perego, M., 1997. Proc. Natl. Acad. Sci. U.S.A. 94:8612-8617; Perego, M. et al., 1996. Proc. Natl. Acad. Sci. U.S.A. 93:1549-1553). Thus, KinA and RapA function to opposite ends. High level phosphorylation of Spo0A (Burbulys, D. et al., 1991. Cell 64:545-552), without which sporulation becomes blocked at an early stage (Hoch, J., 1993. Annu. Rev. Microbiol. 47:441-465), can only occur when RapA becomes inactivated, allowing unimpeded function of the phosphorelay. The inhibitor of RapA is a pentapeptide that is encoded at the 3' end of phrA, the gene immediately downstream of rapA (Mueller, J. et al., 1992. J. Bacteriol. 174:4361-4373; Perego, M. et al., 1996. Proc. Natl. Acad. Sci. U.S.A. 93:1549-1553). The primary translation product of phrA is a 44-amino acid polypeptide that is secreted and cleaved to yield the active pentapeptide. The pentapeptide is transported back into the cell via the oligopeptide permease (Opp) transport system, binds to and inactivates RapA, and lifts the blockade of the phosphorelay (Ishikawa, S. et al., 2002. J. Biol. Chem. 277:20483-20489; Perego, M., 1997. Proc. Natl. Acad. Sci. U.S.A. 94:8612-8617; Perego, M. et al., 1996. Proc. Natl. Acad. Sci. U.S.A. 93:1549-1553; Perego, M. et al., 1994. Cell 79:1047-1055). Spo0F~P is also dephosphorylated by RapB and RapE (Perego, M. et al., 1996. Proc. Natl. Acad. Sci. U.S.A. 93:1549-1553). The mechanism that allows the pentapeptide to accumulate at the appropriate time is unknown.

Figure 5:
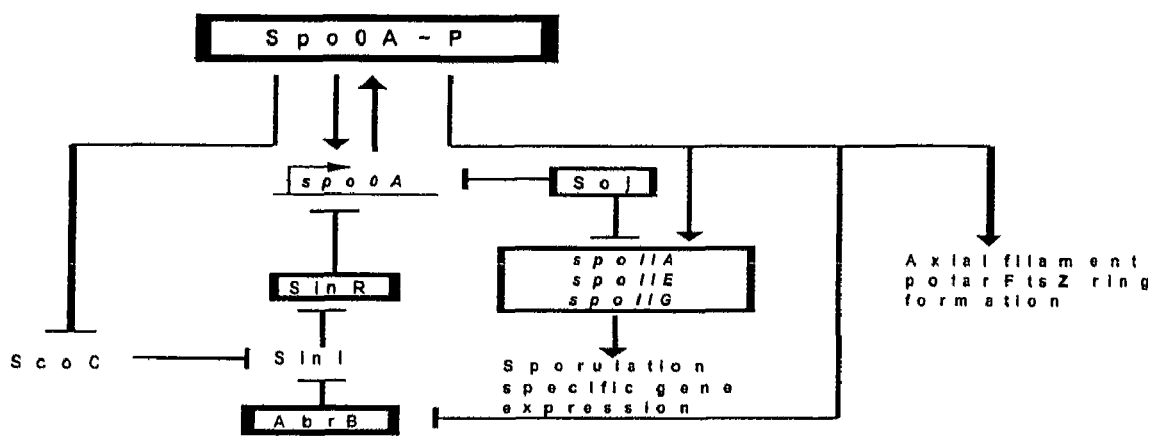
FIG. 5 is a drawing showing effects of various regulatory proteins on early sporulation gene expression. Arrowheads indicate positive effects on transcription or the Spo0A phosphorelay; T symbols indicate negative effects.
Figure 6:
FIG. 6 is a drawing of the promoter and leader region of the ilvB operon.

Several regulatory proteins (e.g., Soj, SinR, SinI, AbrB, ScoC) are known to influence the transcription of the spo0A gene or the activity of the Spo0A phosphorelay or the transcription of Spo0A-dependent genes (FIG. 5). Their activities and those of several other proteins create a complex web of regulatory interactions that collectively determine the rate of transcription of early sporulation genes. Each protein is presumed to respond to a signal, but not all of the signals are known. As detailed below, it is envisioned herein that CodY controls sporulation initiation at least in part by repressing the spo0A gene. Single mutations in any one of the above-mentioned regulators lead to partial derepression of their target genes, but not to constitutive sporulation. A reasonable conclusion would be that most or all genes needed for early sporulation events are subject to multiple forms of regulation and that no single signaling pathway alone determines whether a cell will sporulate, i.e., that each protein senses a different signal and that CodY provides the control mechanism that specifically couples sporulation to nutrient limitation.

The expression of virulence genes is in many ways similar to the adaptation a bacterium undergoes when entering stationary phase or sporulating. Therefore, a featured embodiment of the invention provided herein is a composition for repressing virulence in a Gram positive bacterium, the composition comprising an effective concentration of at least one of a branched chain amino acid or an analog thereof and a cell-permeable precursor or analog guanosine triphosphate (GTP), and a pharmaceutically acceptable salt or buffer, such that the concentration is effective to repress virulence of the bacterium.

Therapeutic Compositions in the Methods of the Invention

A therapeutic compound herein is formulated with a pharmaceutically acceptable carrier or pharmaceutically acceptable buffer or salt, which includes any and all solvents, dispersion media, coatings, antimicrobials such as antibacterial and antifungal agents, isotonic and absorption delaying agents and the like that are physiologically compatible. Preferably, the carrier is suitable for intravenous, intramuscular, oral, intraperitoneal, transdermal, or subcutaneous administration, and the active compound can be coated in a material to protect it from inactivation by the action of acids or other adverse natural conditions. A bacterial infection can be topically treated such as an epithelial infection by *B. anthracis*, or can be treated by local application such as a *B. anthracis* infection of the lung or a streptococcal subcutaneous infection, or can be systemically treated for bacteremia infection. *B. anthracis* and *streptococci* are exemplary, as the bacteria of the infections are envisioned to be any low G+C Gram positive bacteria.

The methods of the invention include incorporation of the therapeutic compound, which is an analog or precursor of a branched chain amino acid (BCAA) or a GTP, guanine or guanosine, into a pharmaceutical composition suitable for administration to a subject. A composition of the present invention can be administered by a variety of methods known in the art as will be appreciated by the skilled artisan. The active compound can be prepared with carriers that will protect it against rapid release, such as a controlled release formulation, including implants, transdermal patches, and microencapsulated delivery systems. Many methods for the preparation of such formulations are patented and are generally known to those skilled in the art. See, e.g., *Sustained and Controlled Release Drug Delivery Systems*, J. R. Robinson, Ed., Marcel Dekker, Inc., NY, 1978. Therapeutic compositions for delivery in a pharmaceutically acceptable carrier are sterile, and are preferably stable under the conditions of manufacture and storage. The composition can be formulated as a solution, microemulsion, liposome, or other ordered structure suitable to high drug concentration.

Dosage regimens can be adjusted to provide the optimum desired response (e.g., a therapeutic response). For example, a single bolus can be administered, several divided doses can be administered over time, or the dose can be proportionally reduced or increased as indicated by the exigencies of the disease situation.

In general, an embodiment of the invention is to administer a suitable daily dose of a therapeutic composition that will be the lowest effective dose to produce a therapeutic effect, for example, mitigation of symptoms. The therapeutic compounds of the invention are preferably administered at a dose per subject per day of at least about 2 mg, at least about 5 mg, at least about 10 mg or at least about 20 mg as appropriate minimal starting dosages. In general, the compound of the effective dose of the composition of the invention can be administered in the range of about 50 to about 400 micrograms of the compound per kilogram of the subject per day.

A physician or veterinarian having ordinary skill in the art can readily determine and prescribe the effective dose of the pharmaceutical composition required. For example, the physician or veterinarian could start doses of the compound of the invention employed in the pharmaceutical composition at a level lower than that required in order to achieve the desired therapeutic effect, and increase the dosage with time until the desired effect is achieved.

In another embodiment, the pharmaceutical composition includes also an additional therapeutic agent. Thus in a method of the invention the pharmaceutical composition can be administered as part of a combination therapy, i.e. in combination with an additional agent or agents. Examples of materials that can be used as combination therapeutics with the compounds for treatment of infectious disease and bacteremias as additional therapeutic agents include: an antibiotic which is an anti-bacterial agent such as a macrolide, a penem or cephem, an aminoglycoside, any of which can be naturally produced or synthetic or semithetic, and are exemplified by amoxicillin, rifampicin, erythromycin; an antibody or an antibody fragment that can bind specifically to an inflammatory molecule or an unwanted cytokine such as interleukin-6, interleukin-8, granulocyte macrophage colony stimulating factor, and tumor necrosis factor-α; an enzyme inhibitor which can be a protein, such as $\alpha_1$-antitrypsin, or aprotinin; an enzyme inhibitor which can be a cyclooxygenase inhibitor; an engineered binding protein, for example, an engineered protein that is a protease inhibitor such as an engineered inhibitor of a kallikrein; an antiviral agent, which can be a low molecular weight chemical, such as acyclovir; a steroid, for example a corticosteroid, or a sex steroid such as progesterone; a non-steroidal anti-inflammatory agent such as aspirin, ibuprofen, or acetaminophen; an anti-cancer agent such as methotrexate, cis-platin, 5-fluorouracil, or adriamycin; a cytokine blocking agent; an adhesion molecule blocking agent; or a cytokine.

An additional therapeutic agent can be a cytokine, which as used herein includes without limitation agents which are naturally occurring proteins or variants and which function as growth factors, lymphokines, interferons particularly interferon-β, tumor necrosis factors, angiogenic or antiangiogenic factors, erythropoietins, thrombopoietins, interleukins, maturation factors, chemotactic proteins, or the like.

A therapeutic agent to be used with the composition of the invention can be an engineered binding protein, known to one of skill in the art of remodeling a protein that is covalently attached to a virion coat protein by virtue of genetic fusion (Ladner, R. et al., U.S. Pat. No. 5,233,409; Ladner, R. et al., U.S. Pat. No. 5,403,484), and can be made according to methods known in the art. A protein that binds any of a variety of other targets can be engineered and used in the present invention as a therapeutic agent in combination with a therapeutic compound of the invention.

An improvement in the symptoms as a result of such administration is noted by a decrease in symptoms of infection such as fever and appearance and number of infective lesions, or other symptoms appropriate to the specific nature of the particular bacterial infection. A therapeutically effective dosage preferably reduces symptoms and frequency of recurrences by at least about 20%, for example, by at least about 40%, by at least about 60%, and by at least about 80%, or by about 100% elimination of one or more symptoms, or elimination of recurrences of the infection, relative to untreated subjects. The period of time of treatment can be at least about one day, one week, one month, at least about six months, or at least about one year.

The invention having been fully described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references, including issued patents and published patent applications, cited throughout this application are hereby incorporated by reference. A portion of the examples herein has appeared in Shivers, R. and A. L. Sonenshein, 2005 Molec. Microbiol. 56:1549-1559, and Joseph, P., Ratnayake-Lecamwasam, M., and A. L. Sonenshein, 2005 J. Bacteriol. 187:4127-4139, both of which are hereby expressly incorporated herein in their entireties by reference.

EXAMPLES

Example 1

Role of CodY and its Mechanism of Action: CodY is a GTP-Activated Repressor

That CodY is a GTP-activated repressor came from several lines of evidence. The dipeptide permease (dpp) operon, the first-known CodY target (Mathiopoulos, C. et al., 1991. Mol. Microbiol. 5:1903-1913), was originally identified based on its inducibility by decoyinine, an inhibitor of GMP synthetase and a well-known inducer of sporulation (Mathiopoulos, C. et al., 1989. Mol. Microbiol. 3:1071-1081; Slack, F. et al., 1991. Mol. Microbiol. 5:1915-1925). Induction by decoyinine was shown to be through CodY and not through AbrB (Ratnayake-Lecamwasam, M. et al., 2001. Genes Dev. 15:1093-1103), a second repressor of dpp (Strauch, M., 1993. In: *Bacillus subtilis* and other Gram positive bacteria: Biochemistry, physiology, and molecular genetics Sonenshein, A. L. et al. (eds.), ASM Press, Washington, D.C., pp. 757-764.). dpp is also inducible by activation of the stringent response (i.e., by severe amino acid limitation), so that inactivation of CodY requires either a drop in GTP or an increase in pppGpp (Ratnayake-Lecamwasam, M. et al., 2001. Genes Dev. 15:1093-1103). The RelA protein is not necessary for the induction of dpp that occurs when cells enter stationary phase and a relA mutant strain can be induced for dpp expression by exposure to decoyinine. Therefore synthesis of pppGpp per se is not required for CodY inactivation, and stringency and decoyinine induce dpp because the GTP pool is reduced.

Analysis of the sequence of CodY revealed that it might contain GTP-binding motifs (G1-G4) typically found in Ras-type small GTPases (Bourne, H. et al., 1991. Nature. 349:117-127), but these motifs are not perfectly conserved (Table 3). Although it lacks GTPase activity, CodY binds GTP (as measured by an in vitro UV-induced crosslinking assay), more avidly than it binds ATP, CTP or UTP (Ratnayake-Lecamwasam, M. et al., 2001. Genes Dev. 15:1093-1103). Further, CodY represses dpp transcription in vitro only when the GTP concentration is relatively high (2 mM). That is, there is strong repression (~80% inhibition of transcription) at a concentration of GTP (2 mM) typically found in rapidly growing exponential phase cells, but there is almost no repression at a concentration of GTP typical of early stationary phase cells (300 µM; Ibid.). Other NTPs had no repression-stimulating activity. The data show that CodY is a GTP-binding protein whose activity as a repressor is greatly enhanced by interaction with GTP.

CodY differs from typical GTPases because CodY has no detectable activity as a GTPase (Ratnayake-Lecamwasam, Ph.D. thesis, Tufts University, 2000), and has relatively low affinity for GTP, since it is activated as a repressor by GTP concentrations in the millimolar range (Ratnayake-Lecamwasam, M. et al., 2001. Genes Dev. 15:1093-1103). In contrast, Ras-type GTPases and FtsZ protein bind GTP in the nanomolar to micromolar range. This difference allows CodY to monitor the pool of GTP inside the cell. That pool is unlikely to ever drop below 100 µM in living cells. For Ras-type proteins, on the other hand, it is the binding of GTP vs. GDP that determines their activity.

Example 2

CodY Controls the Onset of Sporulation

CodY-regulated genes include those that encode extracellular degradative enzymes, transport systems, intracellular catabolic pathways, chemotaxis and motility, antibiotic synthesis, and genetic competence (Burkholder, W. et al., 2000. In: *Prokaryotic development*, Y. Brun et al. (eds.), ASM Press, Washington D.C., pp. 151-166; Debarbouille, M. et al., 1999. J. Bacteriol. 181:2059-2066; Ferson, A. et al., 1996. Mol. Microbiol. 22:693-701; Fisher, S. et al., 1996. J. Bacteriol. 178:3779-3784; Mirel, D. et al., 2000. J. Bacteriol. 182:3055-3062; Serror, P. et al., 1996. J. Bacteriol. 178:5910-5915; Slack, F. et al., 1993. J. Bacteriol. 175:4605-4614; Slack, F. et al., 1995. Mol. Microbiol. 15:689-702; Wray, L. et al., 1997. J. Bacteriol. 179:5494-5501). These responses allow the cell to respond to limitation of its primary nutrients by attempting to find, take up and utilize secondary sources, i.e., these functions allow the cell to continue growing when primary nutrients are exhausted.

To determine whether the GTP-binding ability of CodY also implicate this protein in sporulation regulation cells were grown in a standard medium with an excess of carbon, nitrogen and phosphorus. Wild-type cells in this medium grew to high density but failed to sporulate efficiently unless decoyinine was added (Ratnayake-Lecamwasam, M. et al., 2001. Genes Dev. 15:1093-1103). A codY null mutant, however, grew to stationary phase and then sporulated very efficiently whether decoyinine was added or not (Ratnayake-Lecamwasam, M. et al., 2001).

These data show that at least one gene required for sporulation is repressed by CodY when nutrients are in excess, and that inactivation of CodY allows expression of this gene and sporulation.

Example 3

CodY Controls a Large Group of Genes of Diverse Function

The extent of the CodY regulon was revealed by two sets of DNA microarray experiments (Molle, V. et al., 2003. J. Bacteriol. 185:1911-1922). Wild-type and codY mutant strains were grown in a minimal-glucose medium containing an excess of a 17-amino acid mixture or in a nutrient broth-based medium (DSM). Both conditions lead to strong repression by CodY during exponential growth phase. There was considerable overlap in the potential target genes that were identified. The data show that as many as 125 operons were found to be under negative control by CodY, and another 59 operons appeared to be positively regulated (Molle, V. et al., 2003).

To distinguish between direct and indirect targets of CodY, gel mobility shift assays were used to show that CodY binds to the regulatory regions of the ilvB, ilvD, ybgE, yhdG, yurP, and yufN genes. Of the new potential targets, the most surprising are the large ilvB operon and the ilvA, ilvD and ybgE genes. These genes encode all of the enzymes for synthesis of isoleucine, leucine and valine from threonine and pyruvate.

Example 4

CodY has a Second Effector

A characteristic of CodY repression in vivo is that it occurs in cells growing in a medium comprising a mixture of amino acids, a phenomenon described as "amino acid repression" (Atkinson, M. et al., 1990. J. Bacteriol. 172:4758-4765). Contacting cells with each of the 20 amino acids alone, and in various combinations, was used to determine that only the BCAAs had any substantial effect individually (about 5-fold repression). A similar relationship between BCAAs and CodY activity was observed in *L. lactis* (Guedon, E. et al., 2001. Mol. Microbiol. 40:1227-1239). Expression of genes involved in peptide utilization is under CodY control and is repressed only when peptides containing BCAAs are present in the medium (Guedon, E. et al., 2001. Mol. Microbiol. 40:1227-1239; Guedon, E. et al., 2001. J. Bacteriol. 183:3614-3622).

A test of whether BCAAs have any direct effect on CodY activity was performed. Binding to all of the new target genes, as well as to the dpp promoter region was found to be stimulated significantly by isoleucine or valine (10-30 mM; i.e., in the range of the normal intracellular pool), but not by leucine, and was further stimulated by the mixture of GTP and the BCAAs (see FIG. 1). In all cases, the apparent dissociation constant for binding was substantially below the concentration of CodY inside the cell (4 µM, see below). These data show that CodY performs broad functions in the cell. By regulating gene expression in response to both the GTP level and the availability of certain amino acids, CodY can insure that the cell responds in a coherent way to many types of nutritional stress.

Figure 2:
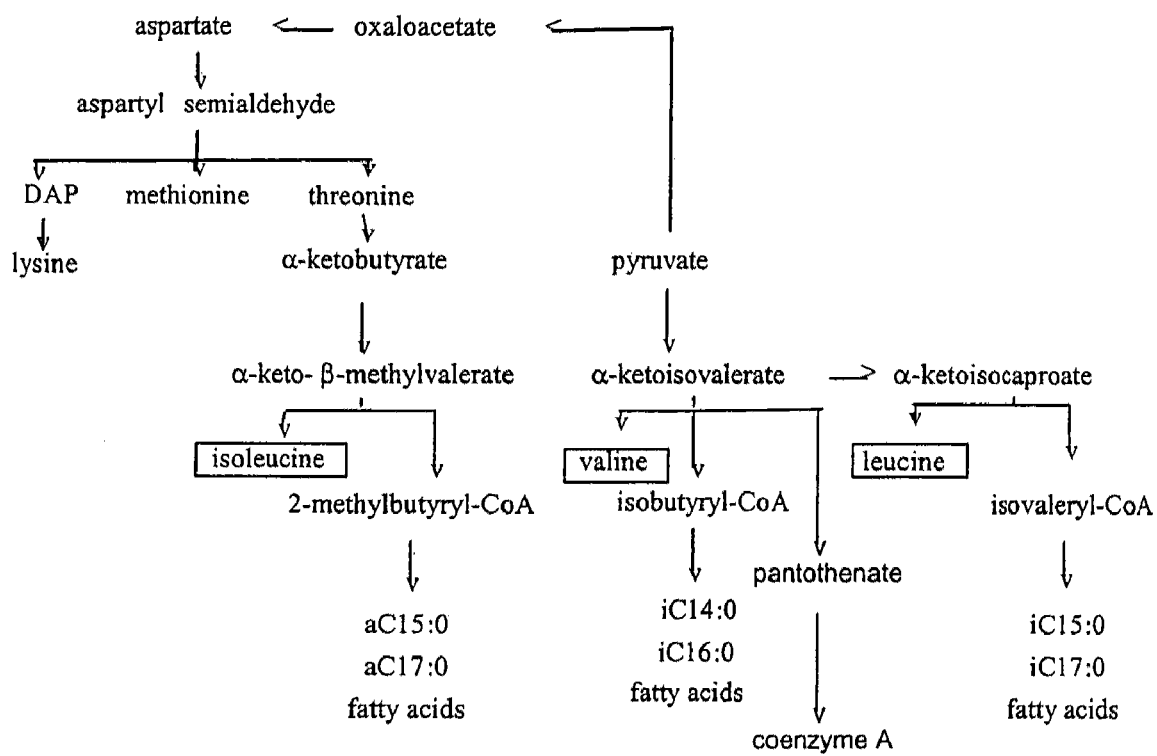
FIG. 2 is a drawing of pathways of biosynthesis of branched chain amino acids and fatty acids in *B. subtilis*.

The BCAAs play a central role in intermediary metabolism. Isoleucine is a member of the aspartate-derived family of amino acids. Its biosynthetic pathway shares several initial steps with the pathways for lysine, methionine and threonine (FIG. 2). Valine is synthesized from pyruvate using enzymes shared with the isoleucine pathway, and leucine is made by a branch of the valine pathway. The keto acids of the BCAAs are the precursors of the branched chain fatty acids (85% of total membrane fatty acids in *B. subtilis* grown at 37° C.; de Mendoza, D. et al., 2002. In: *Bacillus subtilis* and its closest relatives: From genes to cells, Sonenshein, A. L. et al. (eds.), ASM Press, Washington, D.C., pp. 43-56). In addition, α-ketoisovalerate is the precursor of pantothenate and CoA. Both the synthesis of BCAAs and their utilization for fatty acid synthesis are repressed directly or indirectly by CodY (Debarbouille, M. et al., 1999. J. Bacteriol. 181:2059-2066; Molle, V. et al., 2003. J. Bacteriol. 185:1911-1922). Thus, the pools of the BCAAs or their keto acids are biochemically positioned to serve as indicators of the status of overall cellular metabolic sufficiency. For if the cell has ample BCAAs, it is likely to have adequate capacity for synthesizing threonine, methionine, SAM, lysine, DAP, aspartate, oxaloacetate, pyruvate, alanine, PEP, serine, acetyl CoA, citrate, and many other compounds.

The ilvB operon, which encodes most of the ilv enzymes and all of the leu enzymes, now is found to be under two forms of regulation. Transcription that initiates at the ilvB promoter is subject to termination in a leader region when leucine is in excess (Grandoni, J. et al., 1993. J. Bacteriol. 175:7581-7593). Under leucine-limiting conditions, uncharged tRNA$^{Leu}$ binds to the leader mRNA and prevents termination through a T-box mechanism (Freese, E. et al., 1979. J. Gen. Microbiol. 115:193-205; Gonzalez-Pastor, J. et al., 1995. J. Bacteriol. 177:7131-7140). Isoleucine and valine play no role in this regulation. From in vitro results, it is shown that transcription initiation is apparently repressed by CodY in the presence of excess isoleucine and valine, but leucine plays no role in CodY-dependent regulation. Thus, the cell has evolved two distinct mechanisms to regulate the ilvB operon while monitoring all three BCAAs.

Figure 3:
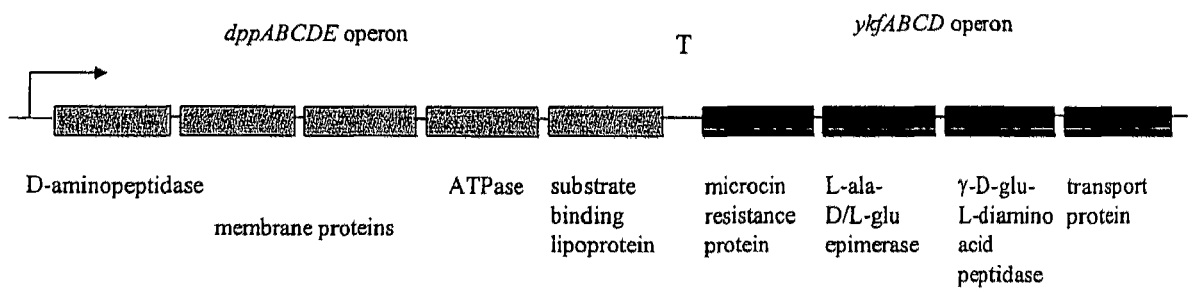
FIG. 3 is a drawing of the structure of the dpp-ykf cluster of genes.

The ykfABCD and yufOPQ operons are indirectly regulated by CodY. Their regulatory regions do not bind CodY in vitro (Molle, V. et al., 2003. J. Bacteriol. 185:1911-1922). They are overexpressed in codY mutant strains, most likely that because they lie immediately downstream of operons (dpp and yufN, respectively) that are direct targets of CodY. It is proposed herein that the terminators of the dpp and yufN operons are not 100% efficient. The ykfABCD operon (FIG. 3) encodes an L-alanine-D/L-glutamate epimerase (YkfB), a γ-D-glutamyl-L-diamino acid peptidase (YkfC), and a transport protein (YkfD) (Schmidt, D. et al., 2001. Biochemistry 40:15707-15715). YkfA is related to a microcin-resistance protein in *E. coli* (Gonzalez-Pastor, J. et al., 1995. J. Bacteriol. 177:7131-7140). These proteins may be involved in recycling of peptidoglycan degradation products. If so, co-regulation of the ykfABCD and dpp operons would be reasonable, since the dpp operon encodes a D-aminopeptidase and a dipeptide uptake system (Cheggour, A. et al., 2000. Mol. Microbiol. 38:504-513; Mathiopoulos, C. et al., 1991. Mol. Microbiol. 5:1903-1913). In *E. coli*, peptidoglycan is recycled during rapid exponential growth phase (Park, J., 1995. Mol. Microbiol. 17:421-426), but not in *B. subtilis* (Mauck et al., 1971. J. Biol. Chem. 246:1820-1827). The co-regulation of the dpp and ykf genes suggests that such recycling in *B. subtilis* occurs only in stationary phase.

Based on homology searches, the yufN, yufO, yufP, and yufQ genes are found herein to encode, respectively, the lipid-linked substrate binding protein, the ATP-binding component, and the permease proteins of an ABC transporter.

Example 5

CodY Represses citB

Synthesis of the Krebs cycle enzyme aconitase (encoded by citB) is regulated by at least two mechanisms. In defined medium containing glucose and glutamine as sole carbon and nitrogen sources, the primary regulator of citB is CcpC, a repressor of the LysR family (Jourlin-Castelli, C. et al., 2000. J. Mol. Biol. 295:865-878). CcpC acts at two binding sites centered at positions −66 and −30 with respect to the transcription initiation site (Fouet, A. et al., 1990. J. Bacteriol. 172:835-844; Fouet, A. et al., 1990. J. Bact. 172:5408-5415; Jourlin-Castelli, C. et al., 2000. J. Mol. Biol. 295:865-878). When cells are grown in a nutrient broth-based medium (DSM), the citB gene is repressed during rapid exponential growth and becomes induced as cell growth slows down (Dingman, D. et al., 1987. J. Bacteriol. 169:3068-3075; Fouet, A. et al., 1990. J. Bact. 172:5408-5415; Ohne, M., 1973. J. Bacteriol. 117:1295-1305; Rosenkrantz, M. et al., 1985. J. Bacteriol. 164:155-164). Mutations in ccpC or its binding sites have little effect on citB expression in DSM (Fouet, A. et al., 1990. J. Bact. 172:5408-5415).

Since citB expression is known to be induced by decoyinine (Dingman, D. et al., 1987. J. Bacteriol. 169:3068-3075), regulation of citB by CodY when cells are grown in DSM was tested. It was found that a codY mutation had only a slight derepressing effect on citB expression (Kim, H. et al., 2003. J. Bacteriol. 185:1672-1680). In a ccpC codY double mutant, however, citB expression was highly derepressed during exponential growth phase, indicating that both CcpC and CodY contribute to repression (Kim, H. et al., 2003). In fact, either one alone was found here to maintain repression, and both repressors must be inactivated in order for the citB gene to be expressed at high level. CodY binds to the citB promoter from positions −10 to +20 (Kim, H. et al., 2003) with a secondary binding site at position −60. Binding is stimulated by GTP (Kim, H. et al., 2003). Since the two repressors respond to different effectors (citrate is the inducer for CcpC, while GTP and BCAA are co-repressors for CodY), citB expression is the result of complex metabolic monitoring.

Example 6

Role of CodY Helix-Turn-Helix Motif

The interaction of CodY with DNA has two aspects, the ability of the protein per se to bind, and stimulation of binding provided by GTP and BCAAs. A C-terminal region of CodY (residues 203 to 222) was identified that appears to form a helix-turn-helix motif and is essential for repression and DNA binding (Serror, P. et al., 1996. Mol. Microbiol. 20:843-852).

Figure 4:
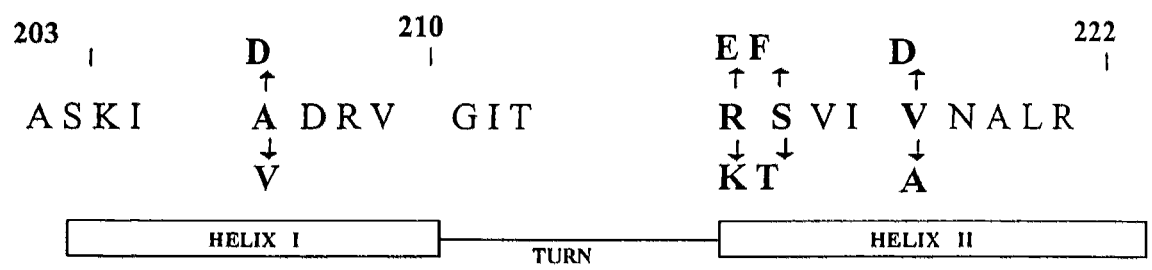
FIG. 4 is a drawing of a helix-turn-helix motif of CodY (SEQ ID NO: 2; see Table 4).

Certain point mutations within the recognition helix led to loss of binding to CodY in vitro and derepression of CodY target genes in vivo (Joseph, P. et al., 2005. J. Bacteriol. 187:4127-4139). Specifically, the mutations A207D and A207V in the positioning helix (I) and R214E, S215F and V218D in the recognition helix (II) caused severe derepression in vivo and more than a 25-fold decrease in affinity of CodY for the dpp promoter in the presence of effectors (FIG. 4, Table 1). On the other hand, the mutations R214K and S215T derepressed expression in vivo only 2-fold, even though they caused a 10- to 20-fold decrease in affinity in vitro (Table 1).

Since the intracellular concentration of CodY is 4 µM, even low affinity versions of the protein are here envisioned to bind with enough affinity in vivo to give partial repression. This result was not obvious, as comparison of several CodY binding sites, some defined crudely by deletion mutations and others defined precisely by DNase I footprinting did not reveal a coherent consensus sequence. The AbrB protein has no consensus sequence for binding, indicating that it recognizes some feature other than primary nucleotide sequence (Xu, K. et al., 1996. Mol. Microbiol. 19:145-158). The only clearly conserved aspect of the nucleotides involved in CodY binding sites is their richness in A+T residues. This surprising result raised the possibility that CodY recognizes a DNA structure rather than a specific sequence. Given the effects of point mutations in the helix-turn-helix structure identified herein (HTH motif), however, it is concluded that CodY interacts with DNA at least partly in a sequence-specific DNA manner through the HTH. In fact, application of a Gibbs Motif Sampler found the weakly conserved sequence CANNATTTTTAAAAATTAT (SEQ ID NO: 1) in four DNase I-protected regions and three other regions that interact with CodY. The specificity of binding through the HTH may not be very strict. A similar consensus sequence has been found for CodY of *Lactococcus lactis* and other species (den Hengst et al., J. Biol. Chem. Jul. 21, 2005 epub ahead of print as manuscript M502349200), and this sequence may substitute for CANNATTTTTTAAAAATTAT (SEQ ID NO: 1) for the methods provided herein.

The effects of GTP and BCAAs at different CodY targets can vary. At several target sites, BCAAs and GTP were each found to have small stimulatory effects on binding (in a gel shift assay), but the mixture strongly stimulates (FIG. 1). At the yhdG regulatory region, however, BCAAs were found to stimulate binding, and GTP seems to have only a small effect either alone or in combination with BCAAs. This result raises the possibility that BCAAs and GTP induce different conformational changes in CodY, and that each conformation can have selective DNA binding properties. Some genes may respond to CodY in its GTP-bound conformation, other genes to CodY in its BCAA-bound conformation, and still other genes to CodY bound to both kinds of effectors. These variations could reflect differences in specificity of binding or differences in affinity of binding.

TABLE 1

Effects of HTH region mutations on CodY binding to the dpp promoter in vitro and on dpp-lacZ expression in vivo

| Mutations | Estimated $K_D$ (nM)[a] | | β-galactosidase expression (Miller units) in mid-exponential cells |
|---|---|---|---|
| | No effectors | +GTP, ILV | |
| WT | 150 | 20 | 6 |
| ΔcodY | NA | NA | 120 |
| A207D | >500 | >500 | 130 |
| A207V | >500 | >500 | 116 |
| R214E | >500 | >500 | 94 |
| S215F | >500 | 350-400 | 12 |
| S215T | >500 | >500 | 150 |
| V218D | >500 | 150-200 | 14 |
| V218A | 250-500 | 100-200 | ND |

[a]CodY binding to the dpp promoter region was tested by gel mobility shift assays in the presence or absence of GTP (2 mM) and isoleucine, valine and leucine (10 mM each). The concentration of CodY that caused 50% of the DNA molecules to be shifted was taken as an approximation of the $K_D$.

Example 7

Intracellular Concentration of CodY

The intracellular concentration of CodY was determined by quantitative immunoblots of crude extracts, using a range of concentrations of pure CodY to calibrate the antibody. CodY was determined herein to represent 0.25% of total soluble protein and to be present at 2500 monomers per cell. The calculated concentration of CodY (using a cell volume of $10^{-12}$ ml) is 4 μM (R. P. Shivers, 2005, PhD thesis, Tufts University, the entire contents of which is hereby incorporated herein by reference). That concentration remains the same during growth and stationary phase (Ratnayake-Lecamwasam, M. et al., 2001. Genes Dev. 15:1093-1103).

Example 8

Toxin Gene Regulation in *C. difficile*

The strong similarity between the CodY-like protein from *B. subtilis* with that of other bacteria of the low G+C Gram positive family raises the possibility that all of these proteins have similar functions and respond to similar effectors. A candidate phenomenon for such conservation of regulation came from analysis of the control of toxin synthesis in *C. difficile*. This organism is the major causative agent of antibiotic-associated diarrhea and pseudomembranous colitis. The two large toxin proteins (Toxins A and B) that are responsible for pathogenesis are synthesized only in stationary phase cells, and their synthesis is inhibited when a rapidly metabolizable carbon source is present in the medium (Dupuy, B. et al., 1998. Mol. Microbiol. 27:107-120).

The first step in analysis was to determine the mechanism by which the toxin genes are expressed. The tox gene promoter sites were identified and stationary phase induction was shown to be mediated at the transcriptional level (Dupuy, B. et al., 1998). The tox gene promoters have non-canonical −10 and −35 sequences, i.e., they might depend on a positive regulator for their transcription or they might be recognized by an alternative form of RNA polymerase. The tox promoters are inactive in vivo unless the cells contain tcdR (txeR), the gene immediately upstream of toxB (Mani, N. et al., 2001. Proc. Natl. Acad. Sci. U.S.A. 98:5844-5849; Moncrief, J. et al., 1997. Infect. Immun. 65:1105-1108). TcdR (TxeR) was purified and found to stimulate binding to the tox promoters by RNA polymerases from *C. difficile*, *B. subtilis* and *E. coli* (Ibid.) and to stimulate transcription from the tox promoters in vitro (Ibid.). More importantly, these effects of TcdR (TxeR) were seen even when RNA polymerase core enzymes rather than the holoenzymes were used (Ibid.). That is, TcdR (TxeR) acts as a sigma factor, recognizing the promoters of the tox genes. Association of a dedicated sigma factor gene with its target toxin genes is a novel mechanism of toxin gene regulation. These genes are located within a 19-kb DNA segment that appears to have been acquired by horizontal gene transfer (Braun, V. et al., 1996. Gene 181:29-38).

Figure 10:
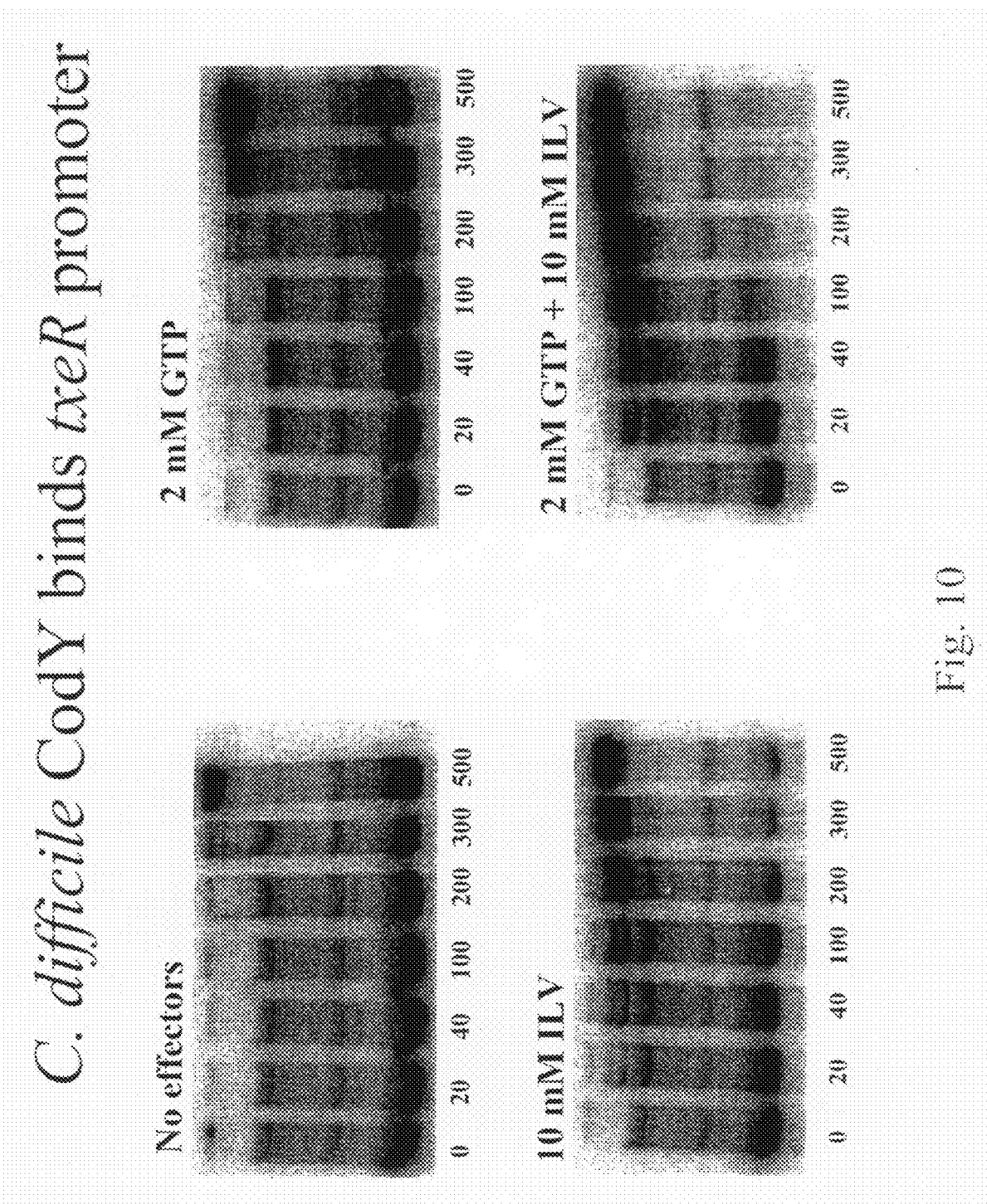
FIG. 10 is a photograph of an electrophoretogram gel mobility shift assay showing that *Clostridium difficile* CodY protein interacts with the promoter region of the txeR (also known as tcdR) gene. The numbers below each lane indicate the concentration (nM) of CodY protein in each binding reaction. In some reactions, GTP (2 mM) and/or a mixture of isoleucine, valine and leucine (10 mM each) was included.

The stationary phase induction of toxin gene expression might be due to relief of repression of the tox promoters at the end of exponential growth phase, or to synthesis or activation of TxeR at that time. It was found that txeR has a low but detectable basal level of expression during rapid exponential growth, and expression of toxin genes is induced as cells enter stationary phase. Moreover, this induction is TcdR (TxeR)-dependent while basal expression is not (Mani, N. et al., 2002. J. Bacteriol. 184:5971-5978). Thus, synthesis of the sigma factor is partly autoregulated (Mani, N. et al., 2002). It is shown here that the CodY is a strong candidate for the regulator responsible for unleashing TcdR (TxeR) synthesis when cells leave exponential growth phase; it may repress tcdR (txeR) alone or txeR and the tox genes independently. Further, *B. subtilis* CodY was found to bind to the txeR promoter region; binding was stimulated by GTP and BCAAs (FIG. 10;

S. S. Dineen, A. Villapakkam, J. Nordman, and A. L. Sonenshein, 2007, manuscript in preparation).

TcdR (TxeR) implications are surprisingly far reaching. Homologs of TcdR (TxeR) are encoded just upstream of toxin or bacteriocin genes in the pathogenic species *C. botulinum*, in *C. tetani*, and in some strains of *C. perfringens*. Thus, the mechanism of toxin gene expression in *C. difficile* is a general mechanism of toxin gene regulation in several major pathogenic *Clostridium* species. Examples herein apply these findings to development of compositions useful for amelioration of bacterial infections.

Example 9

Role of CodY in Initiation of Sporulation

Deletion of codY permits cells to sporulate despite the presence of excess nutrients (Ratnayake-Lecamwasam, M. et al., 2001. Genes Dev. 15:1093-1103), implying that at least one gene required for sporulation is under CodY control. The mutant cells do not sporulate constitutively, but instead grow normally until stationary phase and then sporulate, while wild-type cells under the same conditions remain in stationary phase without sporulating. If CodY were the sole regulator of sporulation, a codY null mutant would sporulate rather than grow; in other words, a codY mutation would be lethal. Thus, while CodY appears to be the major monitor of nutritional sufficiency, other factors contribute to the decision to sporulate. To identify the sporulation gene(s) whose repression by CodY links sporulation initiation to nutrient limitation, complementary biochemical and genetic approaches are used.

Example 10

Genes Involved in Early Sporulation Transcription are Targets of CodY

An N-terminal deletion mutation in spo0A, called sad-67, permits Spo0A to be active without phosphorylation and thereby allows early sporulation gene expression to bypass most of the checkpoints of wild-type cells (Ireton, K. et al., 1993. Genes Dev. 7:283-294). Since the sad-67 mutation and a codY mutation both make Spo0A activity independent of nutrient excess, a protein whose synthesis is regulated by CodY lies on the pathway to Spo0A phosphorylation. Microarray and ChIP-to-chip analyses suggested that spo0A, kinB and the rapA-phrA, rapE-phrE and opp (oligopeptide permease) operons are CodY targets (Molle, V. et al., 2003. J. Bacteriol. 185:1911-1922). In preliminary in vitro experiments, it is found herein that CodY binds to the promoter regions of spo0A, kinB, kinC, spo0B, and spo0F.

Each of the targeted transcription units is analyzed in the following ways: (a) gel shift assays of their regulatory regions in the presence and absence of GTP or isoleucine-valine or both; (b) for those that show binding in the gel shift assays, DNase I footprinting in the presence and absence of effectors; (c) construction of lacZ fusions to the promoter regions of the target operons in wild-type and codY mutant strains and assay of β-galactosidase activity during growth in amino acids-containing medium; (d) primer extension assays of mRNA 5' ends using RNA from wild-type and codY mutant strains; (e) in vitro transcription repression assays using purified CodY, RNA polymerase and effectors.

These five assays establish whether the genes are direct targets of CodY and whether they respond to GTP, to BCAAs, or to both in terms of DNA binding and in vitro transcription. To test the responses of these genes in vivo, cells of the lacZ fusion strains are treated with decoyinine, or are limited for guanine (to create a GTP deficit), or are limited for isoleucine or valine. In addition to the genes whose products affect the phosphorelay directly, other genes may also be relevant targets. For example, expression of citB is essential for Spo0A phosphorylation (Craig, J. et al., 1997. J. Bacteriol. 179:7351-7539) and citB is definitely a CodY target (Kim, H. et al., 2003. J. Bacteriol. 185:1672-1680). These experiments show that several of the genes whose products are needed for full activation of the Spo0A phosphorelay are under CodY control.

Example 11

CodY Target Genes Involving Nutrient Availability

A combination of regulatory proteins, including CodY, prevents sporulation during rapid exponential growth. It is envisioned that a combination of sporulation regulatory mutations would cause lethality in a codY mutant background by derepressing sporulation under conditions of low cell density and nutrient excess. Multiple mutations may derepress sporulation either because they each regulate a unique set of genes whose products are necessary for sporulation or because they are redundant repressors of the same set of genes. Once the combination of mutations that causes lethality is found, mutations are selected that restore viability by blocking the entry into sporulation. The near-lethal phenotype of the sad-67 mutation in spo0A (Ireton, K. et al., 1993. Genes Dev. 7:283-294) predicts a phenotype of lethality. Without being limited by any particular mechanism of action, it is postulated that unregulated or unlimited synthesis of an early sporulation protein (e.g., Spo0A) directs cells to sporulate rather than grow.

Some of the proteins known to regulate Spo0A synthesis and activity are depicted in FIG. 5. Synthesis of AbrB, a repressor of many early stationary phase genes, is itself repressed by Spo0A~P. As a result, when Spo0A is activated by phosphorylation, AbrB synthesis diminishes and the intracellular concentration of AbrB decreases. Even a low level of Spo0A~P is sufficient to repress abrB and thereby permit expression of some stationary phase genes. The histidine kinase that catalyzes this low level of Spo0A phosphorylation is not KinA, the major phosphorelay kinase for sporulation gene expression, and may be KinC (LeDeaux, J. et al., 1995. J. Bacteriol. 177:861-863). The signal that activates KinC is not known, but may be a peptide that accumulates in the medium.

One AbrB target is the sinI gene, whose product is an inhibitor of SinR, a repressor of the spo0A gene. Thus, after repression of sinI is relieved, the intracellular concentration of Spo0A rises, creating a larger pool of molecules susceptible to phosphorylation. A high concentration of Spo0A~P may be required for activation of transcription of the early sporulation operons spoIIA, spoIIG, and spoIIE. KinA seems to be the principal kinase for high level Spo0A phosphorylation. Amplification of the Spo0A~P pool would occur after Rap phosphatases that dephosphorylate Spo0F~P have been inactivated by their respective Phr peptides. Sda (not shown in the figure) is an inhibitor of KinA, and may come into play particularly when DNA damage occurs (Burkholder, W. et al., 2001. Cell 104:269-279). As a result, the cell would not enter the sporulation pathway without having taken the time to repair such damage.

Soj is a component of the chromosome segregation apparatus (Ireton, K. et al., 1994. J. Bacteriol. 176:5320-5329), but has a second role as a repressor of the spo0A, spoIIA, spoIIG, and spoIIE operons (Quisel, J. et al., 2000. J. Bacteriol. 182: 3446-3451). Activity of Soj allows the cell to coordinate expression of Spo0A~P-dependent genes with the partitioning of the two chromosomes that will serve as the genomes of the mother cell and forespore (Quisel, J. et al., 2000). ScoC contributes to repression of sinI and also represses the opp operon (Caldwell, R. et al., 2001. J. Bacteriol. 183:7329-7340; Koide, A. et al., 1999. J. Bacteriol. 181:4114-4117) an important process because oligopeptide permease is needed for uptake of the Phr peptides.

Starting with null mutations in sinR, soj, scoC, and abrB, a set of isogenic strains is constructed that have cumulative null mutations, each preferably marked with a different drug resistance (spc, cat, erm, kan, phi). Each of these regulators has been implicated in control of early sporulation gene expression, mostly influencing the synthesis and activity of Spo0A (Bai, U. et al., 1993. Genes Dev. 7:139-148; Quisel, J. et al., 2000. J. Bacteriol. 182:3446-3451; Caldwell, R. et al., 2001. J. Bacteriol. 183:7329-7340; Strauch, M., 1993. In: *Bacillus subtilis* and other Gram positive bacteria: Biochemistry, physiology, and molecular genetics, Sonenshein, A. L. et al. (eds.), ASM Press, Washington, D.C., pp. 757-764; FIG. 5). In addition, at least AbrB and ScoC are known to have overlapping targets of regulation with CodY (Caldwell, R. et al., 2001. J. Bacteriol. 183:7329-7340; Slack, F. et al., 1991. Mol. Microbiol. 5:1915-1925). As each multiple mutant is created, a codY null mutation is introduced. Without being limited by any particular theory of mechanism of action, it is envisioned that combining a codY mutation with one or more of certain other mutations will be lethal, because Spo0A or some other sporulation-inducing protein will be prematurely synthesized and be active.

The objective is to create a strain whose viability is dependent on codY$^+$. To monitor the timing of early sporulation gene expression in the strain collection, strains additionally carry a Spo0A~P-dependent fusion (spoIIE-lacZ). The mutations will be combined by transformation; the test of lethality is inability to introduce a codY mutation into a given genetic background, by observing no resulting transformants, or by observing only tiny colonies. To control for differences in transformation efficiency, the same cells are transformed with DNA carrying a mutation in a well-characterized gene not known to influence sporulation (e.g., dpp) to show that the same codY mutation can be introduced into other strains using the same DNA preparation.

To verify the lethal phenotype, the order of addition of the markers will be altered to prove that only certain combinations of markers are incapable of being maintained. Thus, in parallel experiments, we have observed that codY and mecA mutations can be individually tolerated by *B. subtilis* cells, but most important, that a codY mecA double mutant is non-viable. Without being limited by any particular theory or molecular mechanism, both CodY and MecA negatively regulate the synthesis or activity of ComK, one of whose activities is to inhibit DNA replication (Dubnau, D. et al., 2002. In: *Bacillus subtilis* and its closest relatives: From genes to cells. Sonenshein, A. L. (eds.), ASM Press, Washington, D.C., pp. 453-472; Serror, P. et al., 1996. J. Bacteriol. 178:5910-5915). Viable combinations include abrB codY soj codY, and scoC codY double mutants and a soj scoC codY triple mutant.

Using a second strategy, a strain is constructed in which the sole copy of codY is under the control of a xylose-inducible promoter (Bhavsar, A. et al., 2001. Appl. Environ. Microbiol. 67:403-410). That strain is constructed to carry the other mutations listed above, to determine the combination that causes lethality. The desired multiple mutant strain would be viable in the presence of xylose but non-viable in its absence.

The goal of looking for synthetic lethality is to use this phenomenon as a means of selecting for mutations that overcome the lethality of the multiply mutant strains and thereby reveal a critical target for CodY. If, for example, we are unable to introduce a codY mutation into a strain that is already deleted both for sinR and scoC, the sinR scoC double mutant is mutagenized, and then the mutagenized culture is transformed with DNA carrying a codY mutation. Any transformants that arise are expected to include mutants defective in sporulation because of the loss of function of a CodY target. As a result, the cells would not obligatorily enter the sporulation pathway and would grow instead. Alternatively, the strain carrying inducible codY is mutagenized and mutants that grow in the absence of inducer are sought. Such spo mutations will be mapped by standard methods, such as marker rescue by an integrative library of *B. subtilis* chromosomal genes. It is expected that the spo0A gene is target of CodY. Once a combination of mutations is found that creates a genetic background incapable of accepting a codY mutation, a spo0A mutation is introduced into that background to test whether the codY mutation can now be accepted.

If the one or more genes identified by the genetic screen has not already been tested for direct interaction with CodY (above), the regulatory regions of these genes are amplified and assayed for their interaction with CodY in gel shift and DNase I footprinting assays.

Example 12

Minimal Conditions Required for Sporulation

The sad-67 mutation in Spo0A has the following effects on gene expression. Genes that normally depend on Spo0A~P for their transcription are expressed despite the absence of Spo0A phosphorylation, despite the fact that the cells are at low density, despite the fact that DNA replication is ongoing, and despite the presence of excess nutrients (Ireton, K. et al., 1993. Genes Dev. 7:283-294). The mutant cells do not complete the process of sporulation under nutrient excess conditions. Rather, they are unable to express the genes that depend on the sigma factors ($\sigma^F$ and $\sigma^E$) whose synthesis is directly stimulated by Spo0A~P (Ibid.). Further, sad-67 mutant cells do sporulate if treated with decoyinine (Ibid.), a drug that reduces guanine nucleotide synthesis and thereby inactivates CodY. This result raises the possibility that only two molecular events, phosphorylation of Spo0A and relief of repression by CodY, are necessary to force cells into the sporulation pathway under conditions where they should be growing exponentially.

To test this possibility, a strain carrying a codY deletion (or codY under the control of a xylose-inducible promoter) and the sad-67 allele of spo0A under the control of the IPTG-inducible spac promoter (Ireton, K. et al., 1993) is grown in rich medium with or without IPTG. The strain also carries a spoIIQ-lacZ fusion in order to monitor the activation of the forespore-specific sigma factor, $\sigma^F$. Cells grown with IPTG will be assayed for sporulation by assay of asymmetric septum formation, by fluorescence microscopy using the membrane-specific dye, FM4-64, for expression of spoIIQ-lacZ, and for spore formation. A codY$^+$ strain will be tested in parallel as a control. If a significant fraction of the codY sad-67 cell population sporulates in rich growth medium in the presence of IPTG, we would conclude that a target of CodY (other than spo0A) normally needs to be expressed in order to get past the earliest stage of sporulation. If the double mutant does not sporulate, mutants that have now acquired ability to sporulate are selected, and the mutations are mapped to identify the unknown factor.

Example 13

Global Role of CodY in Metabolism

Extent of CodY response to GTP is herein expanded to include additional interaction with BCAAs, and the CodY regulon, i.e., the group of genes that respond to CodY regulation, is also greatly broadened. To understand the role of CodY in the context of the overall physiology of the cell, including growth-related metabolism as well as initiation of sporulation, it is envisioned herein that CodY is a broadly active regulatory protein that regulates many genes with a variety of functions and uses two kinds of effectors in order to monitor general changes in nutrient sufficiency. In that sense, CodY may have a function analogous to that of Lrp in Gram negative bacteria.

Example 14

Newly Identified Targets of CodY

Microarray and ChIP-to-chip analyses of CodY-regulated genes revealed new potential targets of CodY to analyze (Molle, V. et al., 2003. J. Bacteriol. 185:1911-1922). Some of these new targets (ilvB, ilvD, ilvA, and ybgE) have already been analyzed in detail (Molle, V. et al., 2003; Shivers, R. et al., 2004. Mol. Microbiol. 53:599-611). Others, such as braB (BCAA transport), acsA (acetyl CoA synthetase), rocABC (arginine catabolism), rocDEF (arginine catabolism), ycgMN (proline catabolism) and guaB (guanine nucleotide biosynthesis) remain to be tested. The guaB gene was the sole protein that co-precipitated with CodY and appeared to be under positive control by CodY in transcript analyses.

To establish whether these transcription units are direct targets of CodY in vivo and in vitro and whether they respond to the availability of GTP or BCAAs or both, the targeted transcription units will be analyzed by: (a) gel shift assays of regulatory regions in the presence and absence of GTP or isoleucine-valine or both; (b) for those that show binding in the gel shift assays, DNase I footprinting in the presence and absence of effectors; and, (c) primer extension assays of mRNA 5' ends using RNA from wild-type and codY mutant strains.

Another goal of these experiments is to collect DNA sequences that interact with CodY. By expanding the number of such sequences a CodY consensus binding sequence is defined (see below).

Example 15

Role of CodY in Regulation of the ilv and bkd Operons

A codY mutant is derepressed both for biosynthesis of BCAAs (Molle, V. et al., 2003. J. Bacteriol. 185:1911-1922; Shivers, R. et al., 2004. Mol. Microbiol. 53:599-611) and for utilization of BCAAs as precursors of branched chain fatty acids (Debarbouille, M. et al., 1999. J. Bacteriol. 181:2059-2066). Given the possibility that CodY plays a direct role in BCAA biosynthesis, the ilvB operon and the other BCAA biosynthesis genes will be tested in greater detail. It is here envisioned that for ilvB regulation there are two modes of regulation, each dependent on a different metabolic signal. It is known that many transcripts that initiate at the ilvB promoter terminate in a leader region when leucine levels are high (Garrity, D. et al., 1994. Genetics 137:627-636; Grandoni, J. et al., 1993. J. Bacteriol. 175:7581-7593). When leucine is limiting, uncharged tRNA$^{Leu}$ accumulates, binds to the leader mRNA (in a region called the T-box) and stabilizes an anti-terminator structure (Garrity, D. et al., 1994. Genetics 137:627-636; Grandoni, J. et al., 1993. J. Bacteriol. 175: 7581-7593). Since isoleucine and valine play no role in this T-box-mediated regulation and since the ilvB operon encodes enzymes for all three BCAAs, there must be another mechanism by which isoleucine and valine influence operon expression. It is here proposed that isoleucine and valine repress ilvB expression through CodY.

To test this hypothesis, lacZ fusions to the ilvB promoter were created that either included or lacked the T-box termination-antitermination sequence. The fusion strains were compared for their response to the addition of an excess of BCAAs (together or individually) and to BCAA limitation (β-galactosidase activity was followed after depletion of one or more BCAAs). Both fusions were induced by limitation of isoleucine or all three BCAAs (Shivers, R. et al., 2004. Mol. Microbiol. 53:599-611). GTP limitation caused by addition of decoyinine also induced both fusions (Ibid.). The effect of a codY null mutation on each response was also measured.

Elimination of the codY gene greatly increased expression from the ilvB promoter (Ibid.). Regulation of the ilvA, ilvD and ybgE transcription units is studied by similar means and may be simpler; these genes lack the complication of the T-box system and may be regulated solely by CodY, isoleucine, and valine. The ilvA product is not involved in leucine biosynthesis and YbgE, the aminotransferase, can probably be replaced by other enzymes of overlapping specificity.

A significant test of the role of CodY is an in vitro transcription assay, in the presence and absence of CodY and effectors. CodY is known to bind near the ilvB promoter and is predicted to block an early step in RNA synthesis when complexed with GTP and/or isoleucine or valine.

The bkd operon encodes 7 proteins that convert the BCAAs to their keto acids (liberating ammonium) and then to the precursors of the branched chain fatty acids (Debarbouille, M. et al., 1999. J. Bacteriol. 181:2059-2066) (see FIG. 2). Regulation of this operon is complex. BkdR, encoded immediately upstream of the operon, is an NtrC-like positive regulator that stimulates transcription from a sigma-54 promoter in the presence of isoleucine or valine (Ibid.).

When a mixture of amino acids is present in the medium, CodY represses the bkd operon, but this repression is overcome by excess isoleucine (Ibid.). These seemingly contradictory phenomena could be explained by several models. First, CodY may be a direct repressor of the bkd operon or of bkdR. In this case, binding of CodY to its target site must be stimulated by a metabolite other than isoleucine and must, in fact, be antagonized by isoleucine. This hypothesis can be easily tested by in vitro assays of CodY binding to the bkd and bkdR promoter regions in the presence and absence of isoleucine. An alternative model is that CodY influences bkd expression indirectly by repressing BCAA biosynthesis. That is, when cells are grown in amino acid-enriched medium, CodY may reduce the intracellular pool of isoleucine and valine, the co-activators of BkdR. This effect would be overcome by specific supplementation with an excess of isoleucine or valine. The second model predicts that CodY would not bind to either the bkd or bkdR promoter regions, a result that would be in keeping with the failure of these regions to show up in CodY co-IP experiments (Molle, V. et al., 2003. J. Bacteriol. 185:1911-1922). The model is tested directly by gel shift assays. The second model can be proved by showing that a codY mutant is derepressed for bkd expression only when the ilv operons are intact. That is, if the cell cannot make BCAAs internally, a codY mutation would have no effect.

Example 16

Role of CodY in Regulation of the guaB Gene

The possible involvement of CodY in the regulation of a guanine biosynthesis gene is investigated because of the role of GTP in CodY activity. The guaB gene will also receive special attention because it may be the first example of a direct target of positive regulation. If guaB proves to be a direct target of CodY by gel shift assays, its response to GTP and BCAAs is tested in vitro and in vivo. To test the response in vivo, a guaB-lacZ fusion strain will be treated with decoyinine or limited for guanine (to create a GTP deficit) or limited for isoleucine or valine. It is not obvious that GTP and BCAAs should affect CodY activity at the guaB promoter in the same way that they influence repression by CodY. From a cell physiology point of view, GTP would be expected to inhibit positive regulation of guaB by CodY.

Example 17

Role of Stringency, BCAAs, and GTP in CodY-Dependent Regulation

Genes that are targets of CodY are induced by amino acid starvation, by inhibition of tRNA charging (i.e., activation of the stringent response), by addition of decoyinine, and by exhaustion of a complex growth medium (Mathiopoulos, C. et al., 1989; Mol. Microbiol. 3:1071-1081; Mathiopoulos, C. et al., 1991. Mol. Microbiol. 5:1903-1913; Slack, F. et al., 1991. Mol. Microbiol. 5:1915-1925; Slack, F. et al., 1993. J. Bacteriol. 175:4605-4614; Slack, F. et al., 1995. Mol. Microbiol. 15:689-702; Ratnayake-Lecamwasam, M. et al., 2001. Genes Dev. 15:1093-1103). Binding of CodY to several targets was found to be stimulated by GTP and by BCAAs. Which of the inducing conditions in vivo change the interaction between CodY and GTP and which change the interaction with BCAAs are unknown, as is the role of RelA in CodY-dependent regulation. To address these questions, fundamental information about the physiology of the cells is first obtained.

DSM is the standard medium for growth and sporulation of B. subtilis. Derived from nutrient broth (primarily boiled beef extract), it is a mixture of amino acids, peptides, fatty acids, and glycerol. During rapid exponential growth in this medium, CodY-regulated genes are generally repressed. These genes are induced as the growth rate slows down and cells make the transition to stationary phase. The key question with respect to CodY activity in vivo is the nature of the intracellular metabolites whose concentrations determine CodY activity.

Table 2 summarizes changes in the nucleotide pools as cells pass from rapid exponential growth (1 hr before the end of rapid growth, indicated as −1) to a transition state (time 0) to stationary phase (1 hr after time 0, indicated as +1). It was observed that the GTP pool decreases drastically from 2.8 to 0.3, but transiently rising to 2.4, as cells left exponential growth.

To measure changes in the pools of free amino acids by ion exchange HPLC, samples of rapidly harvested and washed cells are taken from cultures in DSM at several times between 2 hrs before and 2 hrs after the end of rapid growth and are frozen in dry ice, put through three freeze-thaw cycles, and then sonicated to give complete cell disruption. The soluble extracts are then applied to a calibrated HPLC column and eluted with gradients of salt, pH and temperature. All twenty amino acids found in proteins as well as some by-products of amino acid metabolism (e.g., ornithine, urea, β-alanine, ammonia) are quantitated by ninhydrin staining. Other samples of the same cell cultures serve as sources of RNA for primer extension analysis of dpp and ilvB mRNA levels. A correlation between changes in the intracellular pools of isoleucine or valine and the induction of CodY-repressed genes would provide supporting evidence for a causal relationship. It is also important to correlate the concentrations of these amino acids during rapid exponential phase growth with those (10-20 mM) that activate CodY for repression in vitro.

Elucidating the role of RelA, the pppGpp synthetase, is important in understanding how CodY activity is modulated in vivo. When cells are starved for BCAAs, they should become derepressed for ilv gene expression because uncharged $tRNA^{Leu}$ will accumulate and cause antitermination of the ilvB operon, and because repression by CodY should be at least partially relieved. But uncharged tRNA also induces the stringent response. To determine whether the consequent activation of RelA reduces the GTP pool enough to contribute to inactivation of CodY and resultant induction of ilv, a relA mutant is starved for BCAAs. A B. subtilis relA null mutant, however, is an isoleucine-leucine-valine auxotroph (Wendrich, T. et al., 1997. Mol. Microbiol. 26:65-79), as is a relA mutant of E. coli (Cashel, M. et al., 1996. In: Escherichia coli and Salmonella: Cellular and molecular biology, Second edition, F. C. Neidhardt et al. (eds.), American Society for Microbiology, Washington, D.C., pp. 1458-1496). The reason for this auxotrophy is not known, but could be due to maintenance of a high GTP pool, which would keep CodY active. If so, the BCAA auxotrophy of a relA mutant should be relieved by a codY mutation. Alternatively, transcription of one or more of the ilv operons may require direct intervention by (p)ppGpp or RelA. Analysis of ilv operon expression in each of relA, codY, and relA codY mutants should provide at least partial answers to these questions. A relA missense mutant is not an auxotroph (Inaoka, T. et al., 2002. J. Bacteriol. 184:3923-3930; Ochi, K. et al., 1981. J. Biol. Chem. 256:6866-6875). Therefore, the effect of BCAA limitation in such a mutant is tested without blocking cell growth. The missense mutant is not totally deficient in pppGpp synthesis, however.

Without being limited by any particular theory with respect to the mechanism, it is here proposed that RelA is relevant to CodY-regulated genes simply because its activity reduces the GTP pool. Stringency reduces the GTP pool because GTP is converted to pppGpp, and because production of (p)ppGpp inhibits the enzyme IMP dehydrogenase (Ochi, K. et al., 1981), reducing de novo guanine nucleotide biosynthesis. If the contribution of stringency to relief of CodY-dependent repression is a reduction in the GTP pool (rather than synthesis of pppGpp per se), the effect of stringency should be overcome by addition of guanosine to the medium. Guanosine is converted to GTP by the salvage pathway, which should bypass any known effect of RelA on GTP levels. Guanosine is known to bypass the effect of decoyinine (Ratnayake-Lecamwasam, M. et al., 2001. Genes Dev. 15:1093-1103). Thus, the stringent response in a strain carrying a dpp-lacZ fusion is induced in cultures with or without added guanosine (1 mM), and the activity of β-galactosidase is measured. For the case of genetic competence development, RelA was shown to be required in wild-type cells but became dispensable when cells were treated with decoyinine or deleted for codY (Inaoka, T. et al., 2002. J. Bacteriol. 184: 3923-3930).

TABLE 2

Metabolite pools (mM) measured at intervals during exponential and post-exponential phases

|     | Hour −1 | Hour 0 | Hour +1 |
|-----|---------|--------|---------|
| AMP | 2.1     | 6.8    | 3.5     |
| ADP | 4.4     | 5.7    | 3.3     |
| ATP | 2       | 1.4    | 2.4     |
| GMP | 1.3     | 2.2    | 0.3     |
| GDP | 3.1     | 0.7    | 1       |
| GTP | 2.8     | 0.3    | 2.4     |
| UDP | 1.3     | 1.7    | 1       |
| UTP | 1.4     | 0.4    | 0.9     |
| CTP | 0.5     | 0.4    | 0.9     |
| PEP | 1.7     | 1.1    | 1.7     |
| PGA | 3.4     | 2.2    | 3.0     |
| FDP | 0.8     | 0.7    | 0.2     |

The method by which the stringent response is induced may also be relevant. In previous experiments, cells were treated with pseudomonic acid (mupirocin), a specific inhibitor of isoleucyl tRNA synthetase. In light of the new finding that isoleucine is a potential effector of CodY, a different agent is used, such as serine hydroxamate. Finding that dpp-lacZ induction occurs with serine hydroxamate as well as with mupirocin confirms the role of stringency in CodY inactivation. This issue is also addressed with respect to the ilvB operon. Whether ilvB-lacZ is induced by serine hydroxamate and by mupirocin and whether such induction requires RelA are also tested.

A recent study by Eymann et al. (Eymann, C. et al., 2002. J. Bacteriol. 184:2500-2520) analyzed the stringent response at a global level after treatment of cells with norvaline, an inhibitor of charging of $tRNA^{Ile}$ and $tRNA^{Leu}$. Many genes that we have shown to be repressed directly or indirectly by CodY were induced by norvaline. Prominent among these genes were the BCAA biosynthetic operons. For most of the affected genes, induction by norvaline depended at least in part on RelA (Eymann, C. et al., 2002). Thus, the general view that CodY-repressed genes can be induced by the stringent response has been confirmed, but some exceptions were noted and the possibility of multiple overlapping controls cannot be excluded.

It is envisioned herein that GTP and BCAAs are independent activators of CodY; their effects on CodY are additive. To separate the roles of the two kinds of effectors we use the specificity of decoyinine treatment to reduce the GTP pool without affecting BCAA pools directly. Even partial inactivation of CodY by a reduction in GTP will derepress the ilv-leu operons and consequently change BCAA levels. On the other hand, starving cells for BCAAs has the complication that the stringent response is induced and will lower the GTP level. The best way to separate the effects of GTP and BCAAs in vivo is to isolate a mutant defective in interaction with one of the effectors, but not both. Examples below are directed to the search for such mutants.

Example 18

Three-Dimensional Structure of CodY

Because CodY is the first member of its protein family to be analyzed in detail, fundamental biochemical information is obtained herein about its structure and oligomerization in the presence and absence of effectors in order to elucidate how the effectors influence regulation. For instance, effectors may stimulate binding to DNA by stabilizing formation of dimers or higher order structures.

Overproducing strains of E. coli that express B. subtilis CodY with either a C-terminal or N-terminal 6×His tag were constructed to obtain enough pure protein for crystallization. E. coli strains that express the tagged CodY homologs of B. anthracis, C. perfringens, C. botulinum, S. pneumoniae and C. difficile were also constructed. High-level expression of CodY protein in E. coli is lethal. As a result, we have had to clone the coding sequences under the control of a tightly regulated promoter (araBAD).

To determine the structure of CodY in the presence and absence of DNA (e.g., the 36-bp dpp target site) and in the presence and absence of effectors, crystals were obtained. Those made in the presence of GTP had a different structure than those that formed in the presence of isoleucine and valine or in the absence of effectors (see Blagova, E. et al., 2003. Acta. Cryst. D59:155-157). Data show that the CodY protein co-crystallized in the presence of isoleucine adopted a different conformation (V. M. Levdikov, E. Blagova, P. Joseph, A. L. Sonenshein, and A. J. Wilkinson, 2006. Journal of Biological Chemistry 281:11366-11373, the entire contents of which are hereby incorporated herein by reference). Coordinates obtained can be used in the embodiments of the invention herein to design inhibitors and derivatives with greater affinity for the protein. Thus, it is shown that the protein adopts different configurations in the various conditions, although in both case the fundamental unit was a dimer. The results of more detailed structural analysis are helpful in targeting mutations to residues likely to interact with effectors (see infra).

Example 19

Oligomerization State of CodY in Solution

To determine independently the oligomerization state of CodY in solution (in the absence of DNA), we used non-denaturing acrylamide gel electrophoresis as the method of choice (Bryan, J., 1977. Anal. Biochem. 78:513-519). Purified CodY protein was run in a series of gels at different acrylamide concentrations. Well-characterized marker proteins supplied by Sigma Chemical Corp. were run for comparison. The variation in mobility as a function of gel concentration is a reliable indicator of mass. We used this method successfully to determine the oligomerization states of isocitrate dehydrogenase and citrate synthase (Jin, S. et al., 1996. J. Bacteriol. 178:3658-3660). Confirming evidence is obtained by gel filtration chromatography, again comparing CodY to a series of standard proteins. We used a crosslinking agent, such as dithio-bis-succinimidylpropionate (DSP), to trap various oligomers of CodY. These were resolved by SDS-PAGE after boiling without addition of β-mercaptoethanol (to preserve crosslinks).

Figure 7:
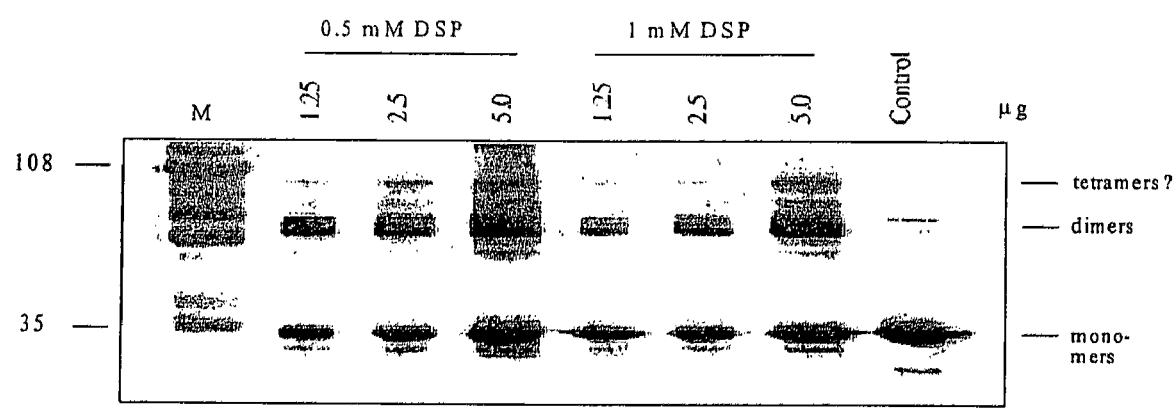
FIG. 7 is a photograph of a gel electrophoretogram immunoblot, showing crosslinking of CodY in vitro with Dithiobis(Succinimidyl Propionate), Lomant's reagent (DSP). Increasing amounts of CodY-containing cell extracts were incubated with DSP (0.5 or 1.0 mM) and then subjected to polyacrylamide gel electrophoresis in the presence of sodium dodecyl sulfate (SDS-PAGE). CodY oligomers were identified by immunoblotting.

Data show that CodY behaved as a dimer in non-denaturing gels and was found as both monomers and dimers in crosslinking experiments (FIG. 7). Higher oligomers were also detected in low abundance. All of these tests are run in the presence and absence of GTP (2 mM) or isoleucine and valine (10 mM each) or all three effectors. If the binding of effectors is weak, however, it may be necessary to incorporate them in the non-denaturing gel and gel running buffer and in the chromatography buffers in order to maintain any novel conformation of CodY that they might induce. For isoleucine and valine this is technically feasible, and for GTP the cost is very high. As a result, the crosslinking experiments are a major component of this analysis, since changes in oligomerization induced by the effectors is preserved by the crosslinking agent during subsequent electrophoresis.

Example 20

Quantitation of Interaction of CodY with Effectors

Two primary assays are used herein for quantitative measurements of interaction of CodY with its effectors: equilibrium dialysis and filter binding. In both cases, radioactive effectors are incubated with CodY and bound and unbound effector is separated. Equilibrium dialysis has the potential to give us the equilibrium dissociation constant, while filter binding can tell us the ON and OFF rates as well as permit competition assays with related metabolites (e.g., GDP, ATP, leucine, ketoisovalerate, ketomethylvalerate). The $K_d$ for GTP is likely to be between 100 and 800 µM, while for BCAAs it probably is in the range of 1-10 mM. Additional candidate precursors and analogs of BCAAs include isovaleric acid, 2-hydroxyisovaleric acid, 2-ketoisovaleric acid, isovaleral, 2-aminobutyric acid, valinol, 2-hydroxy-3-methylvaleric acid, 2-keto-3-methylvaleric acid, 3-methylvaleric acid, 3-methylvaleral, D-valine, D-isoleucine. These exemplary compounds and other analogs and precursors are screened for interaction with CodY as effectors.

The concentration dependence of stimulation of DNA binding by effectors is assessed. At the dpp promoter, GTP at 600 µM increased the fraction of DNA that was bound by a constant concentration of CodY (in a gel shift assay) from 10% to 50%. Titration assays of this type, using varying concentrations of GTP, isoleucine, and valine, provide a measure of the effective concentrations of each of these effectors.

In vitro transcription assays reveal information about CodY-effector interaction. In prior experiments, CodY was able to repress transcription from the dpp promoter at a high GTP concentration (50% repression at about 1.5 mM GTP) (Ratnayake-Lecamwasam, M. et al., 2001. Genes Dev. 15:1093-1103). Careful titration of this effect and analysis of an effect of the BCAAs, alone or in combination with GTP, will give a further indication of the concentrations of effectors that are important for function.

Example 21

CodY Mutants Defective in Interaction with Effectors

The domains of CodY that interact with effectors are explored genetically herein. In addition, X-ray crystallography of CodY-GTP and CodY-isoleucine (or valine) complexes has the potential to point to specific residues that interact with the effectors. The G motifs of CodY (Table 3) are candidates for mutagenesis, even though their conformance to canonical Ras motifs is not strict. Certain families of GTPases, such as FtsZ, have alternative G motifs. In fact, one of the original codY mutations (codY16) is a Gly to Ala mutation, and is located in the putative G1 motif (Slack, F. et al., 1995. Mol. Microbiol. 15:689-702).

To date, several additional mutations in the G1 motif (Thr to Ala, Leu to Ala) have been constructed, and a lysine residue has been inserted between Gly and Thr. All of these mutations caused derepression of dpp transcription in vivo. (The lysine insertion was created in order to make the G1 motif of CodY more like that of Ras. This lysine is critical for Ras GTPase activity; its absence might explain the lack of GTPase activity in CodY). Mutant proteins are purified to test their interaction with GTP and their ability to repress in vitro transcription. The G3 and G4 motifs are targeted by oligonucleotide-directed mutagenesis. The candidate G3 motif (DXXG) is particularly interesting because it lies in the turn of the helix-turn-helix (HTH) motif. Binding of GTP might alter the conformation of the HTH and thereby change the ability of CodY to bind to DNA. Mutant proteins suspected to be defective in GTP binding are purified (as C-terminal 6×His-tagged versions) and tested for interaction with GTP by the UV-induced crosslinking and filter binding assays described above. Mutations in the G3 motif may affect DNA binding directly or as a consequence of reduced affinity for GTP.

These possibilities will be distinguished by comparing binding affinities of mutant and wild-type CodY in the presence and absence of GTP. A mutant protein affected in interaction with DNA will fail to show even the relatively weak binding displayed by wild-type CodY in the absence of GTP, while a mutant with greatly reduced affinity for GTP will bind to the same extent whether GTP is present or not. A mutant CodY specifically defective in interaction with GTP will likely respond normally to BCAAs. If this expectation is realized, a mutant strain defective in GTP binding is then used to separate the effects of GTP and BCAAs on CodY activity in vivo. Data show that the lysine substitution mutation referred to above greatly reduced the response to GTP in vitro, but had no apparent effect on the response to BCAAs.

As part of a general mutagenesis scheme, derepressed mutants are isolated, and are found to be distributed among those that map in the HTH, in the G motifs and elsewhere. The last category may include BCAA binding mutations. A 6×His tagged version of the codY gene is mutagenized by error-prone PCR and then the mutated PCR products are cloned in a plasmid that can integrate into the *B. subtilis* chromosome at the non-essential amyE locus. After transformation of a *B. subtilis* strain deleted for the codY gene and carrying dpp-cat and ilvB-lacZ fusions, blue colonies are selected on plates containing rich medium with chloramphenicol and X-Gal. Colony formation in the presence of chloramphenicol selects for derepression of dpp during exponential growth and production of β-galactosidase indicates derepression of ilvB. To look for mutants specifically defective in response to BCAAs, we will use a strain carrying yhdG-cat and dpp-lacZ fusions, since binding of CodY to the yhdG promoter in vitro responds well to BCAAs but only slightly to GTP. Some mutants will be defective in DNA binding under all conditions. To distinguish them from the desired effector-unresponsive mutants, mutant proteins are purified and assayed for binding in a gel shift assay in the presence and absence of effectors. To eliminate mutants that produce unstable CodY proteins, crude extracts made from cells of each mutant are screened by Western blotting.

If the guaB gene proves to be a target for direct, positive regulation by CodY and to depend on effectors, constitutively active mutant forms of CodY are sought. In principle, such mutants will activate guaB transcription and repress dpp transcription in the absence of effectors. Such a mutant strain carrying a guaB-cat fusion and a dpp-lacZ fusion would grow on glucose-minimal medium containing chloramphenicol and form white colonies. This selection, however, may be ineffective if CodY interaction with the guaB promoter is normally effector-independent or if BCAAs and GTP bind to different domains of CodY. In the latter case, two mutations may be found to be necessary to achieve total effector independence. Constitutively active forms of CodY can also be screened for without positive selection. We transform a strain carrying a dpp-lacZ fusion with an amyE-integrating plasmid carrying a mutagenized population of codY genes. After the mixture is spread on minimal-glucose plates (no amino acids added) containing XGal, white colonies are obtained.

valine and GTP all stimulate binding in the gel shift assay to most, if not all, target DNAs. As the list of CodY targets is expanded, each target gene is characterized for its response to the presence of GTP and BCAAs. Genes that show selective

TABLE 3

Comparison of GTP binding motif-like sequences in CodY homologs.

| Small GTPases Consensus sequences | G1<br>GXXXGKT<br>A    S | ID | G3<br>DXXG | ID | G4<br>NKXD<br>TQ | ID |
|---|---|---|---|---|---|---|
| FtsZ | | | | | | |
| E. coli | LGGGTGTG | 7 | DAFG | 8 | TSLD | 9 |
| CodY | | | | | | |
| B. subtilis | GGERLGTL | 10 | DRVG | 11 | VLNNKFL | 12 |
| B. stearothermophilus | GGERLGTL | 01 | DRVG | 11 | VLNDKFL | 13 |
| B. halodurans | GGQRLGTL | 14 | DRVG | 11 | VLNDKFL | 13 |
| B. anthracis | GGERLGTL | 10 | DRVG | 11 | VLNDKFL | 13 |
| B. cereus | GGERLGTL | 10 | DRVG | 11 | VLNDKFL | 13 |
| S. aureus | GGERLGTL | 10 | DRVG | 11 | VKKEKFL | 15 |
| S. epidermidis | GGERLGTL | 10 | DRVG | 11 | VKKDKFL | 16 |
| L. innocua | GGERLGTL | 10 | DRVG | 11 | VLNDKFL | 13 |
| L. monocytogenes | GGERLGTL | 10 | DRVG | 11 | VLNDKFL | 13 |
| C. hydrogenoformans | GGVRLGTL | 17 | DRVG | 11 | ILNDYFL | 18 |
| D. hafniense | GGERVGTL | 19 | DRVG | 11 | DLNDYLL | 20 |
| S. pneumoniae | SGIRLGSL | 21 | DRIG | 22 | VLISDIF | 23 |
| S. equi | GGMRLGTL | 24 | DRIG | 22 | VINEGIF | 25 |
| S. mutans | GGMRLGSL | 26 | DRIG | 22 | VINEGIF | 25 |
| S. pyogenes | GGMRLGSL | 26 | DRIG | 22 | VINEGIF | 25 |
| E. faecalis | AGKRLGTI | 27 | DEIG | 28 | VLNQQFI | 29 |
| L. lactis | SGMRLGTF | 30 | DKIG | 31 | VLNTGLF | 32 |
| C. difficile | SGQRLGTL | 33 | DRVG | 11 | ILNDKLT | 34 |
| C. perfringens | NGDRLGTL | 35 | DKVG | 36 | ILNEKLM | 37 |
| C. acetobutylicum | NRERLGTL | 38 | DKVG | 36 | ILNDRLL | 39 |
| C. botulinum | NRERLGTL | 38 | DKVG | 36 | ILNDKLL | 40 |

Example 22

Affinity of CodY for DNA

Gel shift assays indicate that CodY binds with widely different affinities to different promoters (e.g., tightly to ilvB, moderately to dpp, weakly to citB). To clarify such differences, which may reflect real differences in the impact of CodY in vivo, quantitative gel shift and filter binding assays are used. In both cases, radioactive target DNA (generally produced by PCR amplification using a radioactive primer) will be incubated with CodY at various concentrations and then separated from unbound DNA. To compare target sites, interaction of each target with CodY is measured individually and in competition experiments.

The gel shift and filter binding assays measure different parameters of interaction. In the gel shift, complexes are incubated for sufficient time to allow equilibration, but, if binding is weak, they may dissociate when the samples are loaded into the wells of the gel. The huge dilution factor inherent in the loading is compensated for, at least in part, however, by the caging effect of the gel. That is, as soon as the complexes enter the gel, dissociation is inhibited by the reduced diffusion of DNA and protein. Thus, this method is a convenient means of assaying and comparing target DNAs, but may not give an accurate measure of equilibrium binding. In the filter binding assay, a time-course of interaction can be followed to quantitate the association rate and competition experiments with unlabelled homologous DNA can be used to quantitate the dissociation rate.

In both cases, the quantitative roles of effectors in modulating CodY-DNA interaction will be assessed. Isoleucine, response to binding to CodY in the presence of one or the other effector will be particularly interesting to analyze in more detail in the manner described in this section.

Example 23

Stoichiometry of Binding

The interaction of CodY with DNA is unusual in that the region of DNA protected against DNase I treatment can vary from 30 to 90 bp, depending on the specific target. Since it has not been possible as yet to identify a clear consensus sequence for binding, it is here envisioned that CodY monomers or dimers associate with each other and with DNA in a variety of ways depending on DNA sequence and structure. To test this idea, the stoichiometry of binding of CodY is determined for at least two target promoters. At the dpp promoter, CodY protects a region of 36 bp, while at the srfAA promoter a total of 87 bp are protected (Serror, P. et al., 1996. Mol. Microbiol. 20:843-852; Serror, P. et al., 1996. J. Bacteriol. 178:5910-5915). It is likely that a different number of CodY monomers is bound in the two cases. If this prediction is confirmed experimentally, two models for CodY binding are considered: (i) interaction of multiple CodY molecules (e.g., dimers) with a reiterated sequence and (ii) spreading of multiple molecules of CodY along the DNA from a primary site of nucleation.

The target DNAs are labeled with $^{32}P$ at the 5' end of one strand and with biotin at the 5' end of the complementary strand. That is, a 5'-biotinylated oligonucleotide and a 5'-$^{32}P$-labeled oligonucleotide are used to amplify the target DNA by PCR. Knowing the specific activity of the σ-$^{32}P$-ATP used for labeling and the amount of the radioactive oligonucleotide, we can deduce the specific activity of the radioactive PCR product. The PCR product will be incubated with purified CodY at various concentrations above and below saturation and the complexes will be captured on streptavidin beads. After we determine the radioactivity of the beads, they will be boiled in SDS to strip off all the CodY. The released protein will be subjected to SDS-PAGE and immunoblotting. By calibrating our anti-CodY antibody against a solution of pure CodY of known concentration, we can determine the number of CodY molecules bound to a given number of DNA molecules in each case. Initial experiments with the double labeling were successful, and showed that the biotinylated DNA was trapped quantitatively by the streptavidin beads.

The stoichiometry assays are carried out both in the absence and presence of effectors, as the presence of effectors changes the number and mobility of complexes in a gel shift assay at certain target sites (see FIG. 2).

Example 24

Definition of Target Sites

The nature of the CodY target has been elusive. While the study of mutant forms of CodY having alterations in the helix-turn-helix domain suggests that CodY recognizes a specific DNA sequence (Serror, P. et al., 1996. Mol. Microbiol. 20:843-852; Joseph, P. et al., 2005. J. Bacteriol. 187:4127-4139) and the CodY HTH motifs from 20 different organisms are 85-100% identical (see, for example, Table 4), no clear consensus sequence has emerged from analysis of all the targets discovered to date. It is hypothesized that CodY does recognize a weakly conserved primary DNA sequence, principally through its HTH domain, but may also see a structure in the DNA, such as an intrinsic bend. So far, only one point mutation in a characterized target site has been isolated. In that case, a T:A to G:C mutation at position +12 of the dpp transcription unit led to substantial derepression in vivo (Slack, F. et al., 1993. J. Bacteriol. 175:4605-4614). By using a Gibbs Motif Sampler program, it was possible to identify the weakly conserved 20-bp sequence CANNATTTTT-TAAAAATTAT (SEQ ID NO: 1) in the regulatory regions of CodY target genes. The dpp mutation would lie at the 18th position of this sequence.

To test the validity of the apparent consensus sequence, the synthetic version of this sequence is cloned and tested for its affinity for CodY in vitro. To generate random mutant versions of the sequence, the DNA synthesis will be doped to give an average of 0.5 mutations per 20 bp. The clones are sequenced to identify the mutations and about 20 point mutants are tested by quantitative gel shift assays.

TABLE 4

A selection of CodY HTH motifs

| Bacterial species | helix 1 turn helix 2 | SEQ ID NO: |
|---|---|---|
| Bacillus subtilis | ASKIADRVGITRSVIVNALR | 2 |
| Listeria monocytogenes | ASKIADRVGITRSVIVNALR | 3 |
| Staphylococcus aureus | ASKVADRVGITRSVIVNALR | 4 |
| Clostridium difficile | ASKIADRVGITRSVIVNALR | 5 |
| Streptococcus pneumoniae | ASVIADRIGITRSVIVNALR | 6 |

Additional point mutations are created in the CodY target site within the dpp promoter region (positions −8 to +27, as defined by DNase I footprinting) by site-directed mutagenesis using overlap PCR. Mutating the −10 region and the nucleotides immediately surrounding the +1 position is avoided. The mutated DNAs (about 400 bp segments that contain the entire promoter region and surrounding DNA) are tested for interaction with CodY by gel shift experiments and are integrated into the B. subtilis chromosome at the amyE locus as fusions to the E. coli lacZ gene. These steps allow assessment of binding in vitro and repression in vivo. The dpp promoter region is used for these experiments because it has one of the smaller CodY binding sites and was the target used for defining the effects of mutations in the CodY HTH domain.

DNA bending, either intrinsic or induced, may characterize CodY target sites. Bent linear DNA has a lower mobility during gel electrophoresis when the bend is near the center of the molecule than when it is near one end (Zwieb, C. et al., 1989. Genes Dev. 3:606-611). To know whether CodY targets have a bent structure, 50-bp fragments corresponding to the CodY binding site and a few surrounding nucleotides from each of several CodY targets are cloned in pBendBlue (Sperbeck, S. et al., 1998. Biotechniques 24:66-68), a vector with reiterated restriction sites. After cleavage with a series of restriction enzymes, the CodY binding site is released as a family of 171-bp fragments in which the center of the site ranges from 35 to 135 bp from one end of the molecule. The behavior of these molecules during electrophoresis in the absence of CodY reveals whether there is any intrinsic curvature. Electrophoresis after binding of CodY suggests whether CodY induces a bend or increases the curvature of the DNA. The difference in mobility of the most bent and least bent forms of the DNA can be used to calculate the bend angle (Zwieb, C. et al., 1989. Genes Dev. 3:606-611). Strauch and colleagues reported that the dpp promoter region is intrinsically bent and that the bend angle is increased by interaction with AbrB (Strauch, M. et al., 1995. Mol. Gen. Genet. 246: 756-760). This assay is used herein to define the site of bending and the bend angle induced by CcpC at the citB promoter.

Example 25

A Second Nutritional Signal for Sporulation

The earliest events in sporulation can be envisioned as follows: key primary nutrients become limiting, the GTP pool or the BCAA pool or both drop and CodY loses activity, permitting expression of genes whose products are designed to support continued growth on secondary nutritional sources, as well as spo0A and the rapA-phrA operon (Mueller, J. et al., 1992. J. Bacteriol. 174:4361-4373; Molle, V. et al., 2003. J. Bacteriol. 185:1911-1922). While cell population density is high enough to respond to signalling peptides and AbrB and ScoC are inactivated, the Spo0A~P-dependent expression of early sporulation genes can in principle occur. But first there is a RapA-imposed delay. By dephosphorylating Spo0F~P, RapA prevents high level accumulation of Spo0A~P. During this intervening period, the cells have the potential to look for secondary nutrients and, if they find them, to continue to grow, albeit slowly. When PhrA pentapeptide accumulates inside the cell and inhibits RapA (Perego, M. et al., 1994. Cell 79:1047-1055), Spo0A~P reaches a level high enough to stimulate transcription of Spo0A~P-dependent genes and sporulation ensues.

We identify herein a fail-safe mechanism involving a metabolite that ties the commitment to sporulation, through the RapA-PhrA system, to the nutritional state of the cell. The sensor of this metabolite is CodY.

This model is tested as follows. In cells growing in DSM, there is a delay of 45-60 minutes between the time of induction of the earliest stationary phase genes (e.g., dpp) and the induction of Spo0A~P-dependent operons, such as spoIIE, spoIIG and spoIIA. Whether a codY mutant shows the same delay in induction of Spo0A~P-dependent genes as does a wild-type strain is tested. To do so, wild-type and codY mutant strains carrying dpp-lacZ and spoIIE-gusA fusions are constructed. Samples of cultures harvested at various times are assayed for both β-galactosidase and β-glucuronidase activities. If the Spo0A~P-dependent class of genes is expressed prematurely in the codY mutant, it is concluded that CodY is the relevant nutritional sensor and that in wild-type cells it continues to repress some genes even while other targets are derepressed.

Such a situation could obtain if different effectors act as co-repressors at different promoters or at different times. For instance, the pools of GTP and BCAAs might drop below their critical levels at different times. As a result, the timing of expression of various genes may differ depending on their affinity for CodY and their sensitivity to each effector. If the codY mutant does not show the delay between stationary phase and spo gene expression, whether addition of any potential nutrients to a wild-type cell that would allow expression of dpp but not spoIIE is then tested. Such nutrients would presumably activate CodY directly or indirectly. If the codY mutant shows no premature expression of Spo0A~P-dependent genes, it is concluded that some other nutrient-sensing regulatory protein controls those genes or that nutrients play no role in the delay. In that case, an attempt is made to block Spo0A~P-dependent gene expression in a codY mutant by adding excess nutrients, such as glycerol, oligosaccharides, oligopeptides, and fatty acids. Then mutations that relieve the sporulation block are sought. These mutants are envisioned to be defective in the hypothetical second nutrient-sensing regulator. The mutations are mapped by conventional methods, allowing the relevant genes to be identified.

The role of the RapA-PhrA system in this delay is tested as follows. A rapA mutant or rapA phrA double mutant sporulates with high efficiency, but it is not known whether the timing of expression of Spo0A~P-dependent genes is speeded up in such mutants. This possibility is tested using the dpp-lacZ spoIIE-gusA double fusion strain, using PhrA pentapeptide, which functions if synthesized intracellularly (Lazazzera, B. et al., 1997. Cell 89:917-925). That is, the phrA gene can be engineered so that the regulatory C-terminal pentapeptide is made as a primary translation product. If the time required for synthesis, secretion, and uptake of the pentapeptide is solely responsible for the delay in induction of Spo0A~P-dependent genes, intracellular synthesis of the pentapeptide in an otherwise wild-type cell should speed up expression of these genes. If no premature expression of the genes is observed, then another factor (such as a nutrient sensing system) must be involved.

Taken together, these experiments indicate whether the pentapeptide model is sufficient to explain the timing of events or whether another factor needs to be invoked. That factor is also have been identified by mutation.

Example 26

Analogs of Guanine, Guanosine, Valine and Isoleucine Repress Toxicity

Non-metabolizable analogs of each of guanine, guanosine, valine and isoleucine are added individually to samples of cultures of various virulent pathogenic Gram positive bacterial strains such as *C. tetani* or *S. aureus*. Toxin production is assayed, and is compared to toxin production by control cultures in the absence of each of the analogs.

For analogs that effectively cause repression of toxin production, effects in combination are analyzed, i.e., combinations of effective analogs, particularly combinations of guanine/guanosine analogs are made with valine/isoleucine analogs, and the individual combinations are each tested for extent of effect on toxin production.

It is expected that addition to cells of a combination of an effective non-metabolizable analog of guanine or guanosine with an effective non-metabolizable analog of isoleucine or valine produces maximal repression of bacterial toxin in culture. The effective analogs, if non-toxic to animals at dosages at which they are effective in bacteria, are candidate therapeutic agents for remediating symptoms of bacterial infection.

Example 27

Test of Repression of Bacterial Toxin Production In Vivo

Animals infected with *C. tetani* or *S. aureus* or another Gram positive bacterial species are treated with combinations of analogs identified as above, as are uninfected control animals. Symptoms of infection such as temperature, bacteremia as determined by bacterial blood count, morbidity, and mortality are measured, and are compared to these parameters in untreated infected animals, and uninfected control animals. It is expected that effective combinations of analogs cause symptoms of bacterial infection to be remediated, i.e., become less severe, and that animal recovery occurs more quickly, in comparison to control untreated infected animals.

Example 28

Figure 8:
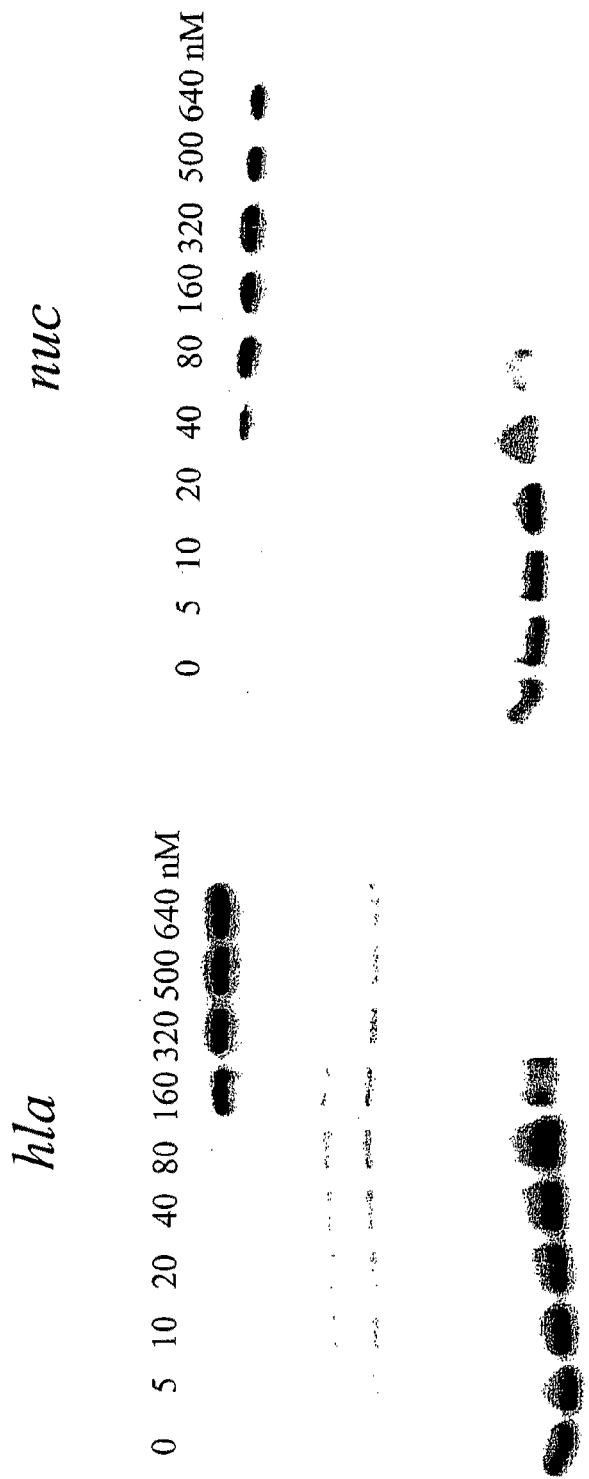
FIG. 8 is a photograph of an electrophoretogram gel mobility shift assay showing that *Staphylococcus aureus* CodY protein interacts with the promoter regions of the hla (alpha-hemolysin) and nuc (nuclease) genes. The numbers above each lane indicate the concentration (nM) of CodY protein in each binding reaction. GTP (2 mM) and a mixture of isoleucine, valine and leucine (10 mM each) were included in each reaction.

Targets of CodY Proteins of *Staphylococcus aureus*, *Bacillus subtilis*, and *Clostridium difficile* and *C. botulinum* in Pathogenic Strains of Bacterial Cells A gel mobility shift assay (FIG. 8; C. D. Majercyk, P. Dunman, G. Somerville, and A. L. Sonenshein, 2007, manuscript in preparation) shows that *Staphylococcus aureus* CodY protein interacts with the promoter regions of the hla (alpha-hemolysin) and nuc (nuclease) genes of this bacterial strain. The numbers above each lane indicate the concentration (nM) of CodY protein in each binding reaction. Further, GTP (2 mM) and a mixture of isoleucine, valine and leucine (10 mM each) were included in each reaction. The data in FIG. 8 show that at a concentration of about 160 nM of CodY protein, the mobility of the target promoters is shifted to that of the complex, for each of the hla and the nuc promoter sequences.

Figure 9:
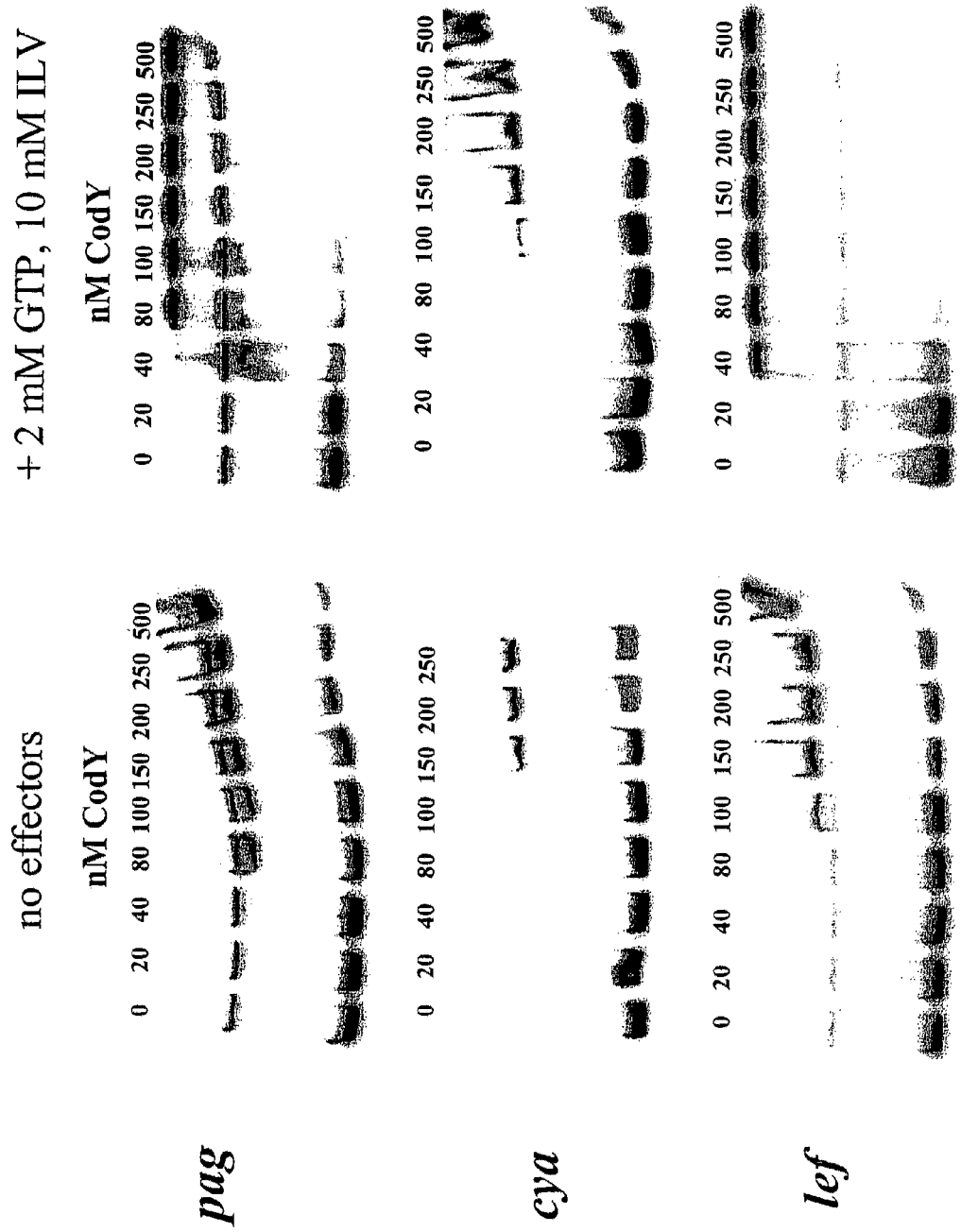
FIG. 9 is a photograph of an electrophoretogram gel mobility shift assay showing that *Bacillus subtilis* CodY protein interacts with the promoter regions of the cya (adenylyl cyclase; edema factor), pag (protective antigen) and lef (lethal factor) genes of *Bacillus anthracis*. The numbers above each lane indicate the concentration (nM) of CodY protein in each binding reaction. In some reactions, GTP (2 mM) and a mixture of isoleucine, valine and leucine (10 mM each) were included.

Further, a gel mobility shift assay seen in FIG. 9 shows that *Bacillus subtilis* CodY protein interacts with the promoter regions of the cya (adenylyl cyclase; edema factor), pag (protective antigen) and lef (lethal factor) genes of the pathogen *Bacillus anthracis* (P. Joseph, W. Van Schaik, A. L. Sonenshein, and A. Fouet, 2007, manuscript in preparation). The numbers above each lane indicate the concentration (nM) of CodY protein in each binding reaction. In some reactions, GTP (2 mM) and a mixture of isoleucine, valine and leucine (10 mM each) were included. The data indicate that for three promoters, CodY of *B. subtilis* binds to the DNA at lower concentrations, when in the presence of GTP and isoleucine (on the right of FIG. 9) than in the absence (on the left of FIG. 9).

Further, a gel mobility shift assay (S. S. Dineen et al., 2007, manuscript in preparation) shows that *Clostridium difficile* CodY protein interacts with the promoter region of the txeR (also known as tcdR) gene (FIG. 10), and the presence of both GTP and isoleucine (lower right panel) enables CodY binding at lower concentrations of protein than the presence of either of these effectors alone, and compared to no effector (upper left panel). The numbers below each lane indicate the concentration (nM) of CodY protein in each binding reaction. In some reactions, GTP (2 mM) and/or a mixture of isoleucine, valine and leucine (10 mM each) was included.

A gel mobility shift assay seen in FIG. 11 shows that *Clostridium difficile* CodY protein interacts with the promoter regions of the *Clostridium botulinum* botR and p47 genes (S. S. Dineen and A. L. Sonenshein, unpublished data). The numbers below each lane indicate the concentration (nM) of CodY protein in each binding reaction. GTP (2 mM) and a mixture of isoleucine, valine and leucine (10 mM each) were included in each reaction.

The genes to which the CodY promoters are shown herein to bind are involved in various aspects of pathogenicity and adverse reactions within an infected subject, such as toxin production, alpha hemolysin, lethal factor and edema. These data show not merely that CodY is a regulatory protein for a variety of Gram positive pathogenic bacteria, but that the pathogenicity per se is under CodY regulation.

What is claimed is:

1. A method for identifying an agent for decreasing expression of virulence factors in a culture of Gram positive bacteria, the method comprising:

contacting a first sample of the culture of the bacteria with an analog of guanine or guanosine, or a non-metabolizable analog of amino acid isoleucine or a non-metabolizable analog of amino acid valine, the analog being present at a concentration effective to activate repression by CodY, wherein the culture comprises at least one strain of the bacteria grown in a chemically defined minimal medium, and wherein a second sample of the culture not so contacted and otherwise identical serves as a control; and analyzing in the first sample and the second sample expression of a CodY regulated gene product, wherein the CodY-regulated gene product is an RNA or a protein, wherein the RNA is an mRNA, wherein decreased expression of the gene product in the first sample compared to expression of the gene product analyzed in the second sample identifies the analog as an agent for limiting expression of virulence factors in cells of the culture of the Gram positive bacteria.

2. The method according to claim 1, further comprising analyzing expression of the gene product in a third sample of the culture of the bacteria contacted with isoleucine and guanine or guanosine which is a positive control, wherein decreased expression in the first sample and third sample compared to the second sample further identifies the analog as the agent.

3. The method according to claim 1, wherein expression in the first sample is at least one selected from the group of: less than about 75% of that in the second sample, less than about 50% of that in the second sample, and less than about 25% of that in the second sample.

4. The method according to claim 1, wherein the sample is a culture of at least one species selected from the group of a *Bacillus*, a *Clostridium*, a *Listeria*, a *Staphylococcus*, a *Streptococcus*, a *Desulfitobacterium*, a *Carboxydothermus*, an *Enterococcus*, a *Lactococcus*, a *Lactobacillus*, and a low G+C DNA content Gram positive bacterium.

5. The method according to claim 4, wherein the *Bacillus* is selected from the group consisting of *B. subtilis, B. anthracis, B. cereus, B. popilliae, B. halodurans, B. stearothermophilus* and *B. thuringiensis*.

6. The method according to claim 1, wherein the mRNA is a transcript of a gene selected from the group consisting of dppA and ilvB.

7. The method according to claim 1, wherein the CodY-regulated gene product is a genetic fusion to a marker gene.

8. The method according to claim 7, wherein the marker gene is selected from the group consisting of a gene encoding a β-galactosidase, a β-glucuronidase, an alkaline phosphatase and a fluorescent protein.

9. The method according to claim 1, wherein the medium further comprises a chemically defined nitrogen source.

10. The method according to claim 1, wherein the medium further comprises at least one amino acid selected from the group consisting of: alanine, arginine, aspartic acid, cysteine, glutamic acid, glutamine, glycine, lysine, methionine, phenylalanine, praline, serine, threonine, and tryptophan.

* * * * *

UNITED STATES PATENT AND TRADEMARK OFFICE
CERTIFICATE OF CORRECTION

PATENT NO.       : 8,202,695 B2                                  Page 1 of 1
APPLICATION NO.  : 11/710339
DATED            : June 19, 2012
INVENTOR(S)      : Abraham L. Sonenshein It is certified that error appears in the above-identified patent and that said Letters Patent is hereby corrected as shown below:

In column 48, line 26, delete "and a" and insert --and the species is a--

In column 48, line 47, delete "praline" and insert --proline--

Signed and Sealed this
Twenty-fourth Day of July, 2012

David J. Kappos
*Director of the United States Patent and Trademark Office*